US010579216B2

(12) United States Patent
Pahud et al.

(10) Patent No.: US 10,579,216 B2
(45) Date of Patent: Mar. 3, 2020

(54) APPLICATIONS FOR MULTI-TOUCH INPUT DETECTION

(71) Applicant: Microsoft Technology Licensing, LLC, Redmond, WA (US)

(72) Inventors: Michel Pahud, Kirkland, WA (US); Kenneth P. Hinckley, Redmond, WA (US); William Buxton, Toronto (CA)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 216 days.

(21) Appl. No.: 15/197,629

(22) Filed: Jun. 29, 2016

(65) Prior Publication Data

US 2017/0277367 A1   Sep. 28, 2017

Related U.S. Application Data

(60) Provisional application No. 62/314,144, filed on Mar. 28, 2016.

(51) Int. Cl.
*G06F 3/0482* (2013.01)
*G06F 3/01* (2006.01)

(52) U.S. Cl.
CPC .......... *G06F 3/0482* (2013.01); *G06F 3/016* (2013.01); *G06F 3/017* (2013.01); *G06F 2203/04808* (2013.01)

(58) Field of Classification Search
CPC .................... G06F 11/1451; G06F 3/04883
See application file for complete search history.

(56) References Cited

U.S. PATENT DOCUMENTS 8,402,391 B1   3/2013 Doray et al.
2002/0185999 A1   12/2002 Tajima et al.
(Continued)

FOREIGN PATENT DOCUMENTS

EP   2990928 A1   3/2016
WO   2011045786 A2   4/2011
WO   2015067962 A1   5/2015

OTHER PUBLICATIONS

"International Search Report and Written Opinion Issued in PCT Application No. PCT/US2017/023691", dated Sep. 13, 2017, 21 Pages.
(Continued)

*Primary Examiner* — Rayeez R Chowdhury
(74) *Attorney, Agent, or Firm* — Alleman Hall Creasman & Tuttle LLP

(57) ABSTRACT

In general, the multi-touch detection implementations described herein use touch detection technologies to provide new and advantageous interactions between users and touch displays using touch, pens and user-wearable devices (UWDs). These new and advantageous interactions include user-associated mobile menus, combined click-through and radial marking menus, menus to automate and improve drawing or manipulation of content on a display, new menus and methods of selecting objects and text on a display, and new interactions with UWDs and touchscreen displays by using UWDs with gestures. In addition, targeted haptic feedback to the UWD of specific users of a display is enabled. In some multi-touch detection implementations menus or tools available to act on object on a display can be ported entirely, or in part, between displays, such as between small and large displays.

20 Claims, 10 Drawing Sheets

(56) References Cited

U.S. PATENT DOCUMENTS

| | | | |
|---|---|---|---|
| 2007/0053367 A1* | 3/2007 | Tyebji | H04W 88/16 |
| | | | 370/401 |
| 2007/0271528 A1* | 11/2007 | Park | G06F 3/0482 |
| | | | 715/810 |
| 2010/0214243 A1* | 8/2010 | Birnbaum | G06F 3/016 |
| | | | 345/173 |
| 2010/0225595 A1 | 9/2010 | Hodges et al. | |
| 2011/0157046 A1* | 6/2011 | Lee | G04G 21/08 |
| | | | 345/173 |
| 2011/0241988 A1 | 10/2011 | Bensler | |
| 2012/0056817 A1* | 3/2012 | Griffin | G06F 3/04886 |
| | | | 345/173 |
| 2012/0113223 A1* | 5/2012 | Hilliges | G06F 3/00 |
| | | | 348/46 |
| 2013/0002578 A1* | 1/2013 | Ito | G06F 3/0488 |
| | | | 345/173 |
| 2013/0069860 A1 | 3/2013 | Davidson | |
| 2013/0288647 A1 | 10/2013 | Turgeman | |
| 2015/0058808 A1 | 2/2015 | John et al. | |
| 2015/0062086 A1 | 3/2015 | Nattukallingal | |
| 2015/0153854 A1 | 6/2015 | Stewart et al. | |
| 2015/0191341 A1* | 7/2015 | Martindale | B67D 1/0888 |
| | | | 222/1 |
| 2015/0261373 A1* | 9/2015 | Smus | G06F 3/0416 |
| | | | 345/174 |
| 2015/0293592 A1 | 10/2015 | Cheong et al. | |
| 2015/0338916 A1 | 11/2015 | Priyantha et al. | |
| 2015/0365784 A1 | 12/2015 | Won et al. | |
| 2017/0277333 A1* | 9/2017 | Bonacina | G06F 3/03545 |

OTHER PUBLICATIONS

Xiaomi, "Mi Band White LED", Published on: Jul. 15, 2015, Available at: http://www.mi.com/in/miband/.

Gummeson, et al., "An Energy Harvesting Wearable Ring Platform for Gestureinput on Surfaces", In Proceedings of the 12th annual international conference on Mobile systems, applications, and services, Jun. 2, 2014, pp. 162-175.

Dietz, et al., "DiamondTouch: a Multi-user Touch Technology", In Proceedings of the 14th annual ACM symposium on User interface software and technology, Nov. 11, 2001, pp. 219-226.

Purcher, Jack, "Microsoft Invents an Advanced 3D Gesture Recognition System that goes far beyond Devices with Displays", Published on: Jan. 16, 2016, Available at: http://www.patentlymobile.com/2016/01/microsoft-invents-an-dvanced-3d-gesture-recognition-system-that-goes-far-beyond-devices-with-displays.html.

* cited by examiner

APPLICATIONS FOR MULTI-TOUCH INPUT DETECTION

CROSS REFERENCE TO RELATED APPLICATION

This application claims the benefit of and priority to provisional U.S. patent application Ser. No. 62/314,144 filed Mar. 28, 2016.

BACKGROUND

The popularity of smartphones, tablets, and many types of information appliances is driving demand and acceptance of touchscreens for various types of electronics. Touchscreens are frequently used where keyboard and mouse systems do not allow a suitably intuitive, rapid, or accurate interaction by the user with the display's content. Many mobile computing devices (e.g., tablets, smart phones, etc.) have touchscreens and use a pen, pointer, or pen type input device in combination with a digitizer component of the computing device for input purposes. Many of these mobile computing devices allow interaction with these touch-sensitive screens with pen and with bare-handed touch or with the two in combination.

Furthermore, touchscreen displays continue to increase in size. Large touchscreens (e.g., greater than eighty inch diagonal) are used as lecture tools in front of audiences or for collaboration between workers, for example. These touchscreens allow a user to manipulate objects displayed by the touchscreen (e.g., by selecting an object, positioning it (e.g., via dragging), and so on.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In general, the multi-touch detection implementations described herein use touch detection technologies to provide new and advantageous interactions between users and touch displays using touch, pens and user-wearable devices (UWDs). These new and advantageous interactions include user-associated mobile menus, combined click-through and radial marking menus, menus to automate and improve drawing or manipulation of content on a display, new menus and methods of selecting objects and text on a display, and new interactions with UWDs and touchscreen displays by using UWDs with gestures to manipulate menus and objects displayed on a display. In addition, targeted haptic feedback to the UWD of specific users of a display is enabled. In some multi-touch detection implementations menus or tools available to act on objects on large screen displays can be ported entirely, or in part, to small screen devices.

Some multi-touch detection implementations described herein are directed to interactive touchscreen displays, particularly ones capable of distinguishing and responding to multiple simultaneous touches (multi-touch), and/or one or more digital styluses (pen and/or touch). While some implementations may be applied to larger interactive digital-whiteboard type displays, other implementations may be applied to smaller versions of interactive displays, such as those incorporated in so-called slate or tablet computers, for example, and even smaller devices such as touchscreen-operated smart phones. In some multi-touch detection implementations described herein menus and tools can be split or distributed between small and large displays.

The multi-touch detection implementations described herein have many advantages. For instance, when large touchscreen displays are used, a processor of a computing device/system can properly interpret an input if multiple touch commands are received. This increases computing efficiency and improves usability by avoiding errors in the interpretation of erroneous and inadvertent inputs from multiple or simultaneous touch commands on a display, such as, for example, a large touchscreen. Additionally, since many multi-touch detection implementations described herein provide menus that move with a user's hand or finger relative to a large display, the user has to reach less and move less to manipulate data on the large display than if the menu or menus were in a fixed location on the large display. In some multi-touch detection implementations, the contours of some of these menus can also be used as drawing tools without having to bring up a specific drawing tool menu or control. By wearing a UWD or other device associated with a specific user that allows each user to be identified, the user experience is improved by allowing personalized menus and capabilities in working with information and objects on the screen including, for example, personalized menus based on a user's past actions or preferences, access to personal data (e.g., images, documents, or other files), and personalized haptic feedback to one or more specific users, including personalized haptic feedback to a UWD of a specific user. Furthermore, since multiple people working on objects and information displayed on a display at the same time with both pen and touch can be distinguished, the time to complete various tasks on the display may be reduced and collaboration between users is improved.

BRIEF DESCRIPTION OF THE DRAWINGS

The specific features, aspects, and advantages of the disclosure will become better understood with regard to the following description, appended claims, and accompanying drawings where:

DETAILED DESCRIPTION

Figure 1:
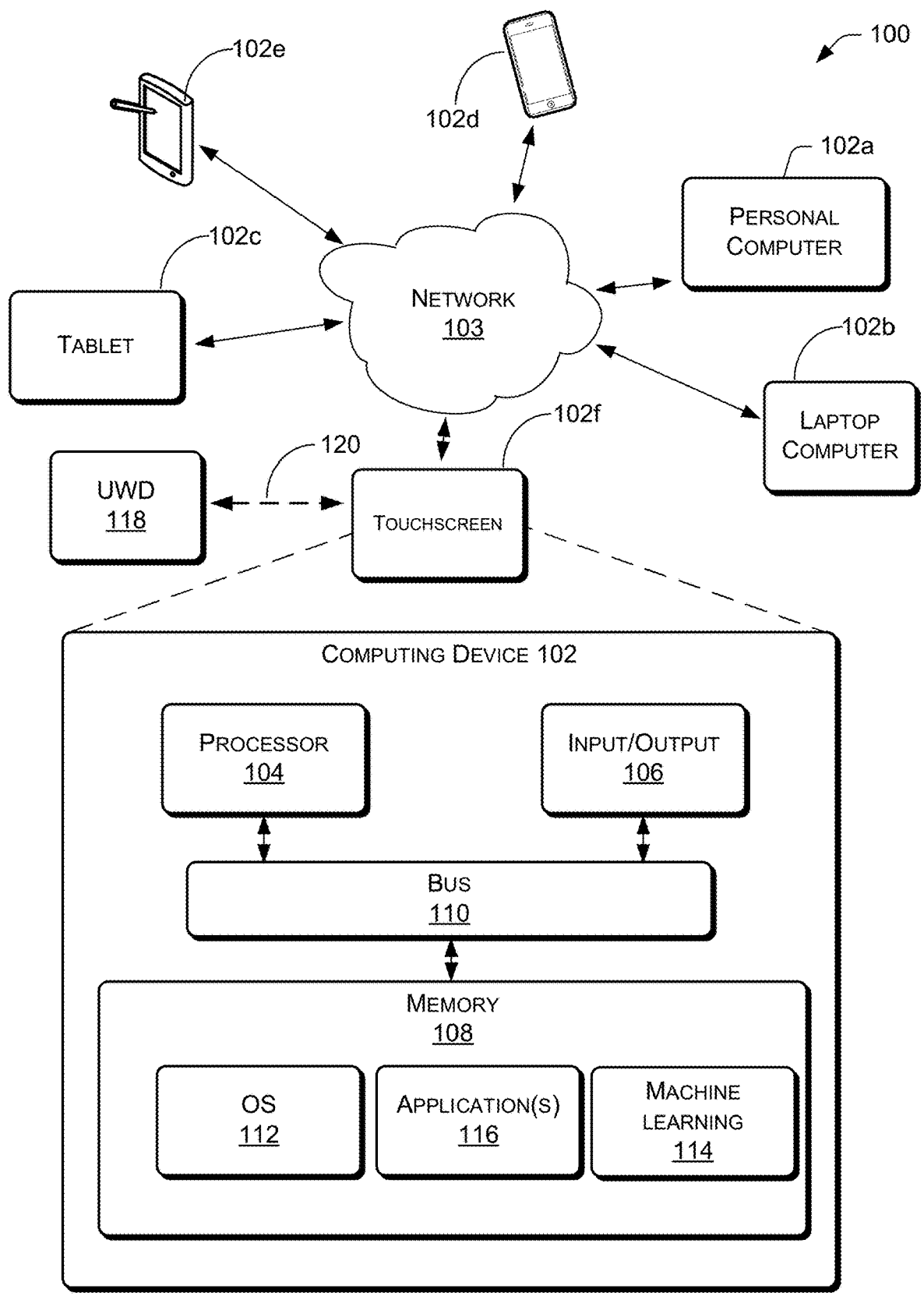
FIG. 1 is a block diagram depicting an exemplary computing environment in which multi-touch detection implementations as described herein may be implemented.

In the following description of multi-touch detection implementations as described herein, reference is made to the accompanying drawings, which form a part thereof, and which show by way of illustration examples by which implementations described herein may be practiced. It is to be understood that other embodiments may be utilized and structural changes may be made without departing from the scope of the claimed subject matter.

1.0 Multi-Touch Detection Implementations

The following sections provide an overview of multi-touch detection implementations, a description of the underlying technologies that enable the multi-touch detection technologies described herein, and a description of an exemplary computing environment. A system in which multi-touch detection implementations described herein can be practiced and various exemplary multi-touch detection implementations are also provided.

As a preliminary matter, some of the figures that follow describe concepts in the context of one or more structural components, variously referred to as functionality, modules, features, elements, etc. The various components shown in the figures can be implemented in any manner. In one case, the illustrated separation of various components in the figures into distinct units may reflect the use of corresponding distinct components in an actual implementation. Alternatively, or in addition, any single component illustrated in the figures may be implemented by plural actual components. Alternatively, or in addition, the depiction of any two or more separate components in the figures may reflect different functions performed by a single actual component.

Other figures describe the concepts in flowchart form. In this form, certain operations are described as constituting distinct blocks performed in a certain order. Such implementations are illustrative and non-limiting. Certain blocks described herein can be grouped together and performed in a single operation, certain blocks can be broken apart into plural component blocks, and certain blocks can be performed in an order that differs from that which is illustrated herein (including a parallel manner of performing the blocks). The blocks shown in the flowcharts can be implemented in any manner.

1.1 Overview

In general, the multi-touch detection implementations described herein use multi-touch detection (e.g., touch by one or more fingers, one or more pens and/or one or more other objects) on a display (or other touch-sensitive device) to provide new and advantageous interactions between users and touch displays or other touch-sensitive devices using touch, pens, user-wearable devices (UWDs) and/or other objects or devices, some of which can be associated with a given user. These new and advantageous interactions include, among others, user-associated mobile menus, combined click-through and radial marking menus, menus to automate and improve drawing or manipulation of content on a display by using the contours of the menu, new methods of selecting and modifying objects and text on a display, as well as new interactions with UWDs and touchscreen displays by using UWDs with gestures. In addition, targeted haptic feedback to the UWD of one or more specific users of a display is enabled. Various implementations described herein can be implemented with a pen, finger/hand, or other objects touching a display.

1.2 Multi-Touch Detection Relative to Displays Using User Wearable Devices

This section provides an overview of an exemplary technique by which a processor of a computing device can identify and classify multiple touches to a display made by a dominant and non-dominant hand of one or more users in order to improve the usability of a large or small display by using various implementations as described herein. This technique, as well as other techniques that can discern touches on a touchscreen display and identify which user and with which hand the user touched the display could equally well be used to enable the various multi-touch detection implementations described herein.

When interacting with an object or device, each hand of a user (herein defined as a person having a right hand and a left hand or having one hand and an opposite hand) may have a different role. For example, the non-dominant hand may be specialized to position a workspace for the dominant hand. In some configurations, an apparatus may distinguish a dominant hand versus a non-dominant hand of a user by receiving wireless signals representative of motion of a device (e.g., a band or ring) worn by the user. The device, herein called a user-wearable device (UWD) may include, for example, motion sensors such as an accelerometer and/or gyro, or type of inertial measurement unit (IMU). Techniques involved may correlate motion of the UWD with touch event(s) of (and detected by) a touchscreen. In some implementations, such techniques may allow detection (or determination) of which user (and which hand of the user), among two or more users, is performing a touch event with the touchscreen (or "display surface", which may comprise any surface that may include a displayed image). It should be noted, however, that other devices, that are not wearable, may perform the functions of the UWDs described herein. These may be, for example, a handheld device, or a sensor-emitter pair, or some other implement that can give the same or similar effect as those provided by a UWD as described herein.

Various terms herein may be used for a touch display device, such as touch screen, touch display, and so on. Unless otherwise specified in a particular context, such terms are substantially equivalent. A touchscreen may include an input device normally layered on the top of an electronic visual display of an information processing system. A user may provide input or control the information processing system during a touch event using simple or multi-touch gestures by touching the display with a special stylus/pen, one or more fingers, one or more hands, or other body parts. The user may, for example, use the touch display to react to what is displayed and to control how it is displayed (for example by expanding (zooming) the text size, selecting menu items or objects, and so on). Herein, a touch event may involve physical touch between the user (e.g., the user's finger(s), hand(s)), or an object such as a stylus and the touchscreen, or may involve a hover event where the user (e.g., the user's finger(s), hand(s)), or an object such as a stylus comes relatively close to (e.g., a few millimeters or a few centimeters) the surface of the touchscreen without touching the touchscreen. In some examples, a touch event may refer to a pressing event that exceeds a certain pressure level (force) on a contact surface, such as that required by a resistive touchscreen. The term "touch event", unless otherwise indicated, refers to a touch event, a hover event, or a combination thereof). Herein, the term "arm/hand" is used to represent any portion of a user's arm or hand, from the shoulder to any of the fingers or thumb. For some examples, a touch event of an arm/hand may involve one or more fingers touching a touchscreen, a side of a hand touching, hovering or passing over a portion of the touchscreen, or a forearm in a particular orientation above the touchscreen. Claimed subject matter is not limited in this respect.

Rather than using a mouse, touchpad, or any other intermediate device, a touchscreen may enable a user to interact directly with displayed objects (e.g., windows, menus, text, drawings, icons, images, and so on) that are displayed. Though some examples herein recite a "screen," techniques herein may be similarly applied to a touch surface without an integrated display, or a display located separately from (or separately projected on) the input surface. For example, UWD sensing techniques may be used in combination with a grip sensor, as well as with a touchscreen (e.g., such as for sensing which hand and/or user makes contact with the rear surface of a grip sensing tablet. Thus, in some examples, a combination of a touch-sensitive surface plus a UWD need not involve a display.

Touchscreens may be used in devices such as game consoles, personal computers, tablet computers, smartphones, large display screens (e.g., situated at the front of a classroom or lecture hall), and so on. A touchscreen may be attached to a computer(s) or used a client device (e.g., as terminals) for networks. A touchscreen may be integrated in the design of digital appliances such as personal digital assistants (PDAs), GPS navigation devices, mobile phones, video games, E-books, and so on.

Various examples describe techniques and architectures for a system enabled to (among other things) detect dynamics of an arm/hand touching a touchscreen or non-touch-sensitive surface or display. For example, a system may detect or determine the impact (e.g., velocity and acceleration in three dimensions) of touch of an arm/hand onto a display or other surface.

In various examples, a system may allow portability, and distributed processing and display, of such techniques on any of a number of types of touchscreens, such as smartphones, slates, large displays, and so on for users wearing one or more UWDs that stream motion sensing data to receivers associated with the touchscreens.

In some configurations, a system may automatically detect, identify, or distinguish among a number of users operating (or being near) a touchscreen. This may be useful, for example, in cases where multiple people are working side by side and/or collaborating on a large touchscreen. In some implementations, cluster information may be used to detect actions of a user even if a hand of the user is not wearing a UWD. In some implementations, menus individually customized to particular users may follow the individual users across multiple devices. In some implementations, a finger clipboard may be used to carry files through the cloud, for example.

Some configurations described herein involve a UWD, which may be a wrist band, bracelet, a patch (e.g., adhesive patch), a glove (e.g., which need not cover the whole hand), and so on. In some cases, a UWD may be a watch or considered to be jewelry. Other examples of a UWD include a band (e.g., bracelet, clasp, bangles, etc.), ring (e.g., one or more on finger(s) or thumb(s)), armband or forearm sleeve or other electronic textiles (e.g., e-clothing), elbow pad or armband worn on upper arm, a mobile device (e.g., phone) affixed or strapped to an extremity, bandage, electronic tattoo with embedded sensors, electronic skin or graft, subcutaneous sensors (e.g., a relatively small module implantable or injected under the skin), electronic fingernail (e.g., stick-on-nail with display and/or sensing ability), or sensors affixed as part of a piercing or other jewelry, among other things.

In any case, a UWD may be configured to wirelessly transmit electronic signals representative of motion of the UWD (e.g., translation, rotation, orientation, speed, velocity, acceleration, etc.) and/or identification (ID) of the wearer of the UWD. Such ID may comprise identifying information for a particular user or for a group of users. For example, identification indicating a user is a faculty member and not a student may allow particular user-privileges or data access for faculty users not afforded to students. A UWD may include a memory device, a transmitter and/or transceiver, and/or a processor, for example, though claimed subject matter is not limited in this respect. In some implementations, a user may wear more than one UWD (e.g., a band on the non-dominant hand and a ring on the dominant hand). In some implementations, the UWD can also wirelessly receive electronic signals from a computing device that may be controlling a display or other device the user is using. For example, the UWD could receive haptic feedback for actions the wearer of the UWD takes on objects displayed on the display. This haptic feedback can be at the same time or after a touch event, or may not be related to a touch event at all. In some implementations the UWD may be configured to wirelessly received electronic signals representative of commands that cause the UWD to perform some function, such as, for example, to vibrate in response to the command or to provide an audible alert.

In some examples, an ID may be in the form of a globally unique identifier (GUID) or MAC address or other unique string derived from the connection (pairing) of the UWD with the display or other proximal device. In some implementations, a username of a user and/or user information (e.g., user preferences) may be found on the Internet or Cloud (e.g., username not stored in the UWD) by using a GUID of the UWD. In some particular examples, detecting or establishing an ID need not require any additional hardware beyond sensors and a wireless connection.

In some configurations, when a finger of a user touches a touchscreen, a "touchdown" event (sometimes named "pointer-pressed") may be produced by an application programming interface (API). This event may be responsive to the finger having touched the touchscreen. In some configurations, the event may involve information that may allow a processor, for example, to determine which hand of the user, or which user among a number of users, has touched the touchscreen. For example, the information may include identification data of a user. The data may be stored in a UWD worn by the user. The data may be wirelessly communicated to a processor (e.g., a processor of the touchscreen) (i) subsequent to or in parallel with the touchdown event, (ii) from time to time or periodically, (iii) when the user (and the UWD) is within a particular distance from the touchscreen, or (iv) at the beginning of a session of use of the touchscreen, just to name a few examples.

The touchdown event may involve information that may allow a processor to determine the intensity of the touch. As described below, such determination may be based, at least in part, on motion detected using inertial measurement devices, such as an accelerometer, gyroscope, compass, and so on.

In some example configurations, actions of the processor, and associated actions of the touchscreen (e.g., what objects or images may be displayed subsequent to the event), may be based, at least in part, on the determination of (i) which hand of the user, or which user among a number of users, has touched the touchscreen, (ii) orientation of the hand at the time of touch, (iii) orientation of the other users' hands at the time of touch, and (iv) the intensity of the touch, among other things. For example, if a particular user is determined to have touched the touchscreen, then a menu that is customized (e.g., a priori, or based on most-recently-used commands and tools by the particular user, on the present device or elsewhere) to the particular user may be displayed. In another example, if a dominant hand of a user is determined to have touched the touchscreen, then the touchscreen may resultantly display objects or images different from the case where the non-dominant hand was determined to have touched the touchscreen. In yet another example, if the intensity (e.g., touch impact—how hard the user touched the screen) is determined (or detected) to be above a particular threshold, then the touchscreen may resultantly display objects or images different from the case where the intensity is determined (or detected) to be below the particular threshold. In yet another instance, there might be more than one threshold.

Herein, the phrase "modifying at least one object displayed by a touchscreen" refers to a touchscreen (e.g., or other type of display or surface) changing what (e.g., windows, menus, icons, graphical objects, text, and so on) or how (e.g., brightness and/or contrast of particular portions of the touchscreen) it displays the objects or display background. In some examples, a system may use indirect inputs (e.g., as in desktop computing, where a device on the desk triggers actions on the separate display). In other examples, a system may use interaction(s) on a projected surface. A surface need not be a display, per se, such as a case where an image is projected onto a surface such as a wall or desk.

A system, which may include a touchscreen, a processor of the touchscreen, and a UWD worn by a user, may wirelessly receive signals from the UWD. Signals representative of motion of the UWD (and thus associated motion of the user) may include shapes, profiles, spikes, etc. For example, signals representative of acceleration plotted as a function of time may include an acceleration pulse (e.g., spike or sharply-profiled pulse) that may indicate a touchdown event. This is because peak acceleration may occur at the time when the user's finger or hand touches a surface, such as the touchscreen. Accordingly, a pulse of an acceleration signal may indicate such a touchdown event. Such a pulse may have a pulse width (e.g., full width at half max (FWHM)) of about 100 milliseconds or less, though claimed subject matter is not so limited.

In some configurations, if the width of an acceleration pulse is below a (predetermined) threshold and its height (amplitude) is above a detection threshold, then the processor of the system may determine that there is a correlation between the touchdown event and the acceleration pulse produced by the UWD. Thus it may be likely that the hand wearing the UWD (the non-dominant hand may be wearing the UWD, but this need not be the case) just touched the touchscreen (or other surface). The processor of the system (e.g., via an API) may subsequently initiate a hand-detection event that will have information about which hand just touched (e.g., non-dominant hand in this case), user information (since the API "knows" which UWD motion produced the spike in the accelerometer at that time), and the intensity of the touch (based on the shape of the spike (pulse)). In some examples, an API may return a contact ID and finger position (which may be sensed by a standard touch API, for example). For illustrative purposes, an input provided by the non-dominant hand is referred to herein as a non-dominant input and an input provided by the dominant hand is referred to herein as a dominant input.

As just described, in some configurations a UWD that is worn by a hand that performs a touch may produce an acceleration pulse and/or other motion rate change. The UWD worn on a hand that performs a touch may measure the acceleration profile when the touch occurs. (In some implementations, the UWD may stream transmitted sensor data while a processor controlling a display measures the acceleration profile or other motion parameters based, at least in part, on the sensor data. Similarly, in some implementations, a controller on a touch display can inform the UWD when a touch event is received and then the UWD can inform the display controller when it measures a spike in the acceleration of the UWD and other motion parameters.) On the other hand, the hand that is not wearing a UWD may instead perform a touch. Even though the hand not wearing the UWD performed the touch and the hand wearing the UWD did not perform a touch, the UWD may nevertheless produce an acceleration profile. This is because motion of one part of the user may transfer (e.g., "shock" wave, weight shift, etc.) to another part of the user. The difference is as follows: the UWD of a hand that performed a touch may produce a relatively spiked profile having a relatively large magnitude. But the UWD worn on the other hand (that did not perform the touch) may produce a relatively flattened pulse in some implementations In some configurations, a user may wear multiple UWD's on the same arm (i.e. a ring and a band). For example, in such a case a system may be able to determine the orientation of the finger and the wrist to create more complex gestures. The motion signals provided by each device can also be combined in this case to more confidently or more sensitively detect spikes in the motion signal.

In some configurations, a UWD may be worn on the non-dominant hand, but the system may be automatically informed where the UWD is worn based, at least in part, on user preferences for a specific user. Such user preferences may be provided from memory located in the Cloud or part of a system, input by the user, or may be gathered directly from the UWD (e.g., user settings stored on the UWD). Default settings (e.g. users typically wear watches on the left hand) may also be used in case of incomplete knowledge. In another instance, machine learning, and/or cameras, etc. may be used to determine where the UWD is worn. In yet another instance, there may also be a mix of such approaches to determine where the UWD is worn. Configurations described herein may be applied to slates (e.g., not limited to large displays and smartphones) or any type of device (with or without a display) that can be touched.

In examples herein, though an element, such as a user, an object, finger, hand, UWD, processor, and so on, may be stated in the singular, claimed subject matter is not so limited. Thus for example, unless otherwise stated, more than one of such elements may be implied.

1.3 Exemplary Operating Environment

The environment described below constitutes one exemplary operating environment for practicing various multi-touch detection implementations as described herein and is not intended to limit the claims to any one particular operating environment. Other environments may be used without departing from the spirit and scope of the claimed subject matter.

FIG. 1 illustrates an exemplary environment 100 in which exemplary processes as described herein can operate. In some examples, the various devices and/or components of environment 100 include a variety of computing devices 102. By way of example and not limitation, computing devices 102 may include devices 102a-102f, which may be interconnected via a network 103 that may comprise the Internet or the Cloud (e.g., a computing cloud), for example. Although illustrated as a diverse variety of device types, computing devices 102 can be other device types and are not limited to the illustrated device types. Computing devices 102 can comprise any type of device with one or multiple processors 104 operably connected to an input/output interface 106 and memory 108, e.g., via a bus 110. Computing devices 102 can include personal computers such as, for example, desktop computers 102a, laptop computers 102b, tablet computers 102c, telecommunication devices 102d, personal digital assistants (PDAs) 102e, a touchscreen(s) 102f, electronic book readers, wearable computers, automotive computers, gaming devices, measurement devices, etc. Computing devices 102 can also include business or retail oriented devices such as, for example, server computers, thin clients, terminals, and/or work stations. In some examples, computing devices 102 can include, for example, components for integration in a computing device, appliances, or other sorts of devices.

In some examples, some or all of the functionality described as being performed by computing devices 102 may be implemented by one or more remote peer computing devices, a remote server or servers, or a cloud computing resource. In some examples, a computing device 102 may comprise one or multiple processors 104 to receive kinematic and/or user identification from a UWD via input/output 106, which may comprise a wireless receiver, for example.

In some examples, as shown regarding touchscreen 102f, memory 108 can store instructions executable by the processor 104 including an operating system (OS) 112, and programs or applications 116 that are loadable and executable by processor 104. The one or more processors 104 may include one or more central processing units (CPUs), graphics processing units (GPUs), video buffer processors, and so on. In some implementations, machine learning module 114 comprises executable code stored in memory 108 and is executable by processor 104 to collect information, locally or remotely by computing device 102, via input/output 106. The information may be associated with one or more of applications 116. Machine learning module 114 may selectively apply any of a number of machine learning decision models stored in memory 108 (or, more particularly, stored in machine learning 114) to apply to input data. For example, machine learning may be involved in processes involving the processor interpreting or determining user actions based, at least in part, on information received from a UWD 118, which may wirelessly communicate with a device (e.g., 102) that operates touchscreen 102f via wireless communication path 120. In some implementations, touchscreen 102f may comprise a display surface (e.g., any surface such as a wall, table, etc.) associated with processor 104. For example, touchscreen 102f may be a wall with an image displayed thereon by a projector operated by a processor.

Though certain modules have been described as performing various operations, the modules are merely examples and the same or similar functionality may be performed by a greater or lesser number of modules. Moreover, the functions performed by the modules depicted need not necessarily to be performed locally by a single device. Rather, some operations could be performed by a remote device (e.g., peer, server, cloud, etc.).

Alternatively, or in addition, some or all of the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

In some examples, computing device 102 can be associated with a depth camera, which may be used to measure distances from the camera to various portions of an image captured by the camera. In some cases, individual pixels of the image may have associated distance data specifying the distance from the camera to the portion of the image corresponding to the respective pixel. In some examples, computing device 102 can be associated with a camera capable of capturing images and/or video and/or a microphone capable of capturing audio. For example, input/output module 106 can incorporate such a camera and/or microphone. Captured images of users of a touchscreen, for example, may be compared to images in a database of users stored in memory 108, and such comparing may be used, in part, to identify the users. Audio of speech may be compared to audio in a database of users stored in memory 108, and such comparing may be used, in part, to identify the users. Such identifying may be used in conjunction with identify information provided by UWD worn by one or more of the users. Memory 108 may include one or a combination of computer readable media.

Computer readable media may include computer storage media and/or communication media. Computer storage media includes volatile and non-volatile, removable and non-removable media implemented in any method or technology for storage of information such as computer readable instructions, data structures, program modules, or other data. Computer storage media includes, but is not limited to, phase change memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that can be used to store information for access by a computing device.

In contrast, communication media embodies computer readable instructions, data structures, program modules, or other data in a modulated data signal, such as a carrier wave, and/or other transmission mechanism. As defined herein, computer storage media does not include communication media. In various examples, memory 108 is an example of computer storage media storing computer-executable instructions. When executed by processor 104, the computer-executable instructions configure the processor to, among other things, receive kinematic data for a UWD during a touch event for a touchscreen performed by a user; and modify at least one object displayed by the touchscreen based, at least in part, on the received kinematic data.

In various examples, an input device of input/output (I/O) interfaces 106 can be an indirect input device (e.g., a mouse, keyboard, a camera or camera array, etc.), or another type of non-tactile device, such as an audio input device.

Computing device(s) 102 may also include one or more input/output (I/O) interfaces 106 to allow the computing device 102 to communicate with other devices. Input/output (I/O) interfaces 106 can include one or more network interfaces to enable communications between computing device 102 and other networked devices such as other device(s) 102. Input/output (I/O) interfaces 106 can allow a device 102 to communicate with other devices such as user input peripheral devices (e.g., a keyboard, a mouse, a pen, a game controller, a voice input device, a touch input device, gestural input device, and the like) and/or output peripheral devices (e.g., a display, a printer, audio speakers, a haptic output, and the like).

1.4 Exemplary System

Figure 2:
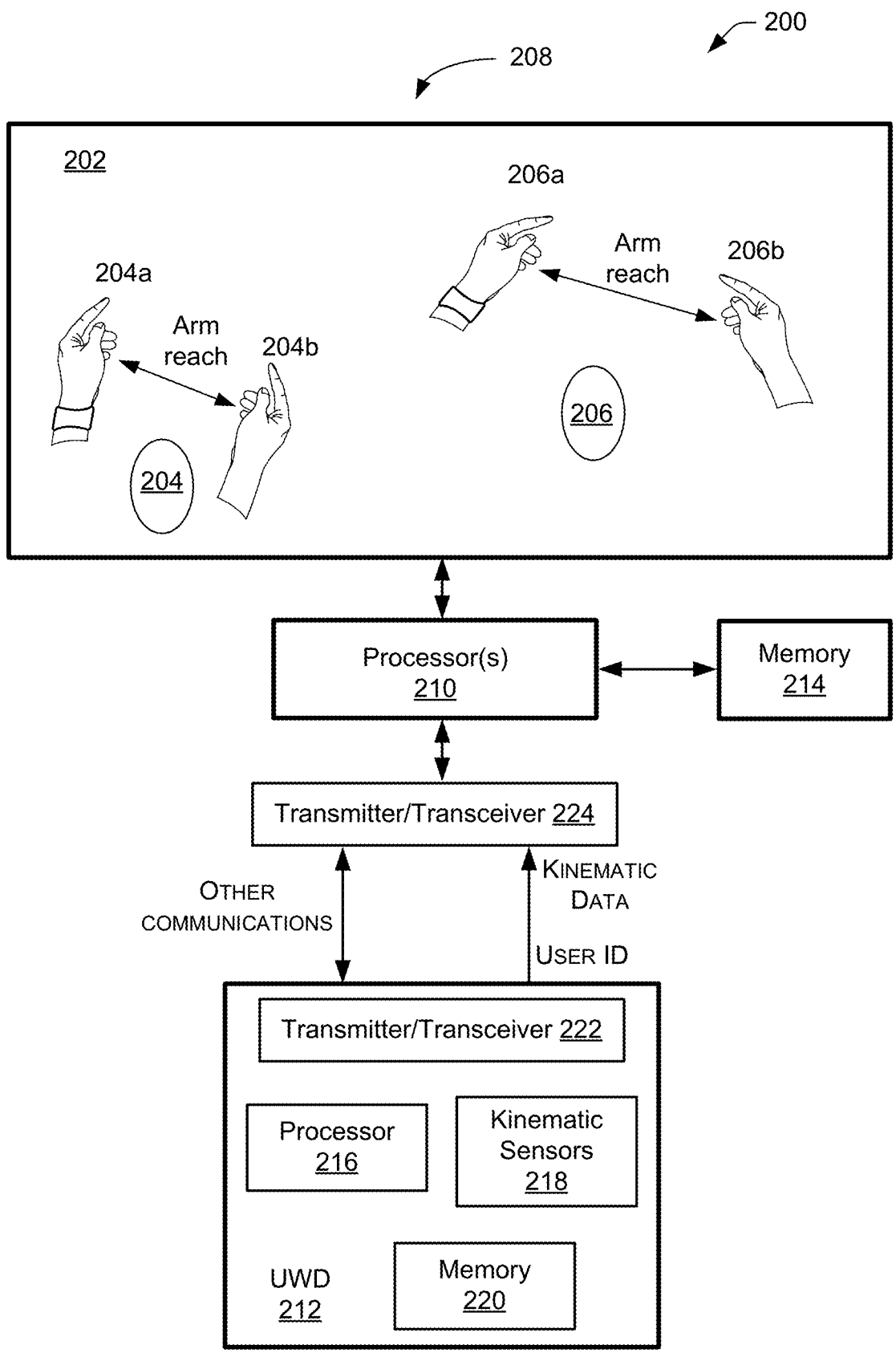
FIG. 2 is a schematic representation of an exemplary system that includes a touchscreen and users of the touchscreen, according to exemplary multi-touch detection implementations as described herein.

FIG. 2 is a schematic representation of a system 200 that can be used to practice various multi-touch implementations as described herein. The system 200 includes a touchscreen 202 and users 204 and 206 of the touchscreen, according to example configurations. User 204 has a dominant hand 204a and a non-dominant hand 204b. User 206 has a dominant hand 206a and a non-dominant hand 206b. (It is to be noted that a user may wear a UWD on a non-dominant hand or dominant hand). Such hand assignments are merely examples, and a dominant or non-dominant hand may be a left hand or a right hand of a user. Though a finger of the hands is illustrated as approaching and/or touching the touchscreen, examples include cases where more than one finger, a side or back of a hand, or the thumb may approach or touch a touchscreen, and claimed subject matter is not limited in this respect. Also, right and left hands of a user may cross one another in their approach or touch of a touchscreen. Moreover, right and left hands of multiple users may cross one another in their approach or touch of a touchscreen.

System 200 may further comprise a processor 210 associated with touchscreen 202 and a UWD 212. In various configurations, a "system" may be considered to include any combination of things identified as being in system 200, which is a particular example for which claimed subject matter is not so limited. For example, in some configurations, a system may be considered to be touchscreen 202 and processor 210 (e.g., excluding the users and UWD). Again, claimed subject matter is not so limited.

Herein, unless specifically noted, "processor" may include one or more processors. Processor 210, which may be similar to or the same as processor 104 of computing device 102, illustrated in FIG. 1, may be used to operate touchscreen 202. For example, processor 210 may execute code to allow touchscreen 202 to display objects generated by any of a number of applications, which may also be executed by processor 210. A memory 214, which may be local (e.g., hard-wired in packaging of touchscreen 202 and/or processor 210) or remote (e.g., in a wired or wireless computer network), accessible to processor 210 may store such executable code or applications.

UWD 212 may be communicatively coupled (e.g., wired or wirelessly) to processor 210 (and thus to touchscreen 202). UWD 212 may include a processor 216, kinematic sensors 218, a memory 220, and a transmitter/transceiver 222. In some examples, UWD 212 may further include a heartbeat monitor, light sensors, cameras, depth cameras, and so on. Kinematic sensors 218, which may comprise inertial sensors, gravitational sensors, compasses, accelerometers, barometric sensors, force sensors or strain gauges, bend or flex sensors, sensors that detect compression of a material, and so on, may generate kinematic data that includes position, velocity, and/or acceleration of the UWD with respect to an inertial coordinate system (e.g., in reference to touchscreen 202) and/or with respect to the local coordinate system of the wearable itself. UWD 212 may transmit kinematic data via transmitter/transceiver 222 to processor 210 via a transmitter/transceiver 224. Memory 220 may store personal and/or identifying data of individual users. Such data, for example, may include user preferences for operating various applications (e.g., menu or display parameters), identification (e.g., ID number, name, user name, and so on) to allow for distinguishing the user from other users, and historical data of kinematic behavior (e.g., physical characteristics of touch events that are typical for the user). In some configurations, the GUID of the UWD may be transmitted while the rest of the data comes from the Cloud or from system 202, or a combination thereof. In some configurations, a user of UWD 212 or system 200 has to "opt-in" or take other affirmative action before personal data may be used or stored by the UWD or system 202, or another system in communication with UWD or system, or the cloud.

In some configurations, processor 210 may transmit information (e.g., "other communications", as identified in FIG. 2) to UWD 212, such as handshaking data or signals that notify presence or various actions performed by processor 210 and/or UWD 212.

As pointed out above, a touch event may be, among other things, one or more hands or one or more fingers physically contacting a touchscreen. By any of a number of techniques described herein, system 200 may be able to identify particular users 204 and 206, and these users may have different attributes, such as different heights, different arm-length reaches, and so on. Such attributes may be stored by in memory 214, 220, or the Cloud (e.g., 103). For example, user 206 may be taller than user 204 and may be able to reach higher on touchscreen 202 toward the top 208 of the touchscreen, as compared to user 204. User 206 may also have a wider reach so that, for a given standing or sitting position in front of touchscreen 202, hands 206*a* and 206*b* may be able to cover a wider portion of touchscreen 202 as compared to user 204.

In some configurations, subsequent to determining which hand of a user is dominant and non-dominant, system 200 may modify any of a number of features or objects displayed by touchscreen 202. Such features or objects may include, among other things, windows, menus, icons, brightness and/or contrast of particular portions of the touchscreen, graphical objects, text, and so on. For example, because hand 204*a* is the dominant hand of user 204, a region of touchscreen 202 around the location of user 204 or around a touch event initiated by hand 204*a* may display objects appropriate for action by a dominant hand, which may be different from those for a non-dominant hand.

In some configurations, subsequent to determining which hand of a user is left and right (e.g., independent of which hand is dominant and non-dominant), system 200 may modify any of a number of features or objects displayed by touchscreen 202 based on such determination. For example, the portion of the touchscreen that is determined to be relatively near (or within arm's reach, for example, based on size information about the user, handedness of the user, and so on) the left hand may display differently as compared to the portion of the touchscreen relatively near the right hand.

In some configurations, using motion information provided by UWD 212 worn by user 204 or 206 (or any possible additional users), the user may initiate a touch event involving two or more fingers, hands, or any combination thereof to virtually "grab" an object displayed by touchscreen 202 and rotate and/or translate the displayed object in real time as the user's hands or fingers (or wrist, etc.) correspondingly rotate and/or translate. For example, such three-dimensional ("3D") manipulation of displayed objects may then be dragged and dropped to various parts of the display of the touchscreen.

In some configurations, 2D orientation information provided by UWD 212 worn by user 204 or 206 (or any possible additional users) may be used in an example case where fingers/hand may behave as if touching a (virtual) knob on the touchscreen and turning the knob by rotating the fingers/hand to the left or right.

In some configurations, orientation information provided by UWD 212 worn by user 204 or 206 (or any possible additional users) may be used to control displayed information. If the user reaches to a relatively higher point (e.g., resulting from a steeper tilt of the UWD), a particular menu may be displayed. If the user touches a relatively lower point, a different menu may be displayed. Additionally, rotation of the user's hand may produce additional menus. UWD orientations may enable a display of multiple menus or different information, according to the location of the touch relative to the user position.

In some configurations, orientation information provided by UWD 212 worn by user 204 and/or 206 (or any possible additional users) may be used to modify touch events. In a similar fashion to retrieving new or deeper information by additional pressure, a user may orient a hand relative to a touch point (such as changing the tilt and/or rotation of the hand, or the horizontal direction of the hand) as a gesture to receive additional data related to the touched object, for example. Pressure and orientation can also be combined in one instance.

In some configurations, using kinematic information provided by UWD 212 worn by a user, the user may magnify (enlarge) displayed objects. In some cases, a user may magnify an object while performing 3D manipulation of that object and/or other objects (e.g., gesture in the air). For example, user 204 may initiate a touch event comprising physical contact with touchscreen 202 or comprising a hover over the touchscreen. The touch event may include the user performing a pinching or spreading motion of their hands and/or fingers in space or on the surface of the touchscreen. Such motion may correspond to negative or positive magnification of objects displayed by touch screen 202.

In some examples, a touch event may comprise a hand of the user hovering above a touchscreen. In such a case, a processor may track motion of the hovering hand of the user and modify at least one object displayed by the touchscreen based, at least in part, on the motion of the hovering hand of the user. For example, the motion of the hovering hand may comprise rotation of the hovering hand. Modifying object(s) displayed by the touchscreen may involve rotating the object(s) corresponding to the rotation of the hovering hand.

In some configurations, by using kinetic data provided by UWD 212 worn by a user, system 200 need not include a camera, depth camera, or other image/video-capturing device to detect or measure motion of one or more of the users. Such configurations may also allow system 200 to detect, using UWD 212, a user approaching and leaving (e.g., walking toward or away from) touchscreen 202.

In some configurations, UWD 212 may provide personal information about each user (e.g., after an "opt-in" selection by each user), or may provide identification of each user so that processor 210 may subsequently retrieve from memory 214 such personal information.

In some configurations, UWD 212 may allow personal information or user-preference settings to transfer across multiple devices (e.g., devices other than touchscreen 202 and processor 210). For example, if a user has a particular work-in-progress activity displayed on touchscreen 202, then the user may transfer (e.g., leave touchscreen 202 and walk) over to another computing device or display and the work-in-progress activity may likewise transfer to the other computing device or display (e.g., the work-in-progress activity may be displayed by the other device). Icons, personal menus, display settings, and so on, may similarly be transferred across multiple devices. Memory 220 of the UWD may store data that enables such transfer. In another configuration, the UWD may act as an identifier of the user for the different devices so that the different devices may retrieve (e.g., from another device on a network, a server, Internet, or Cloud) icons, personal menus, settings, work-in-progress, and so on.

All of the above-described configurations and capabilities can be used to implement various advantageous interactions between users, displays and UWDs. These are described in more detail with respect to Section 1.5.

1.4.1 Timing of Touch Events

Figure 3:
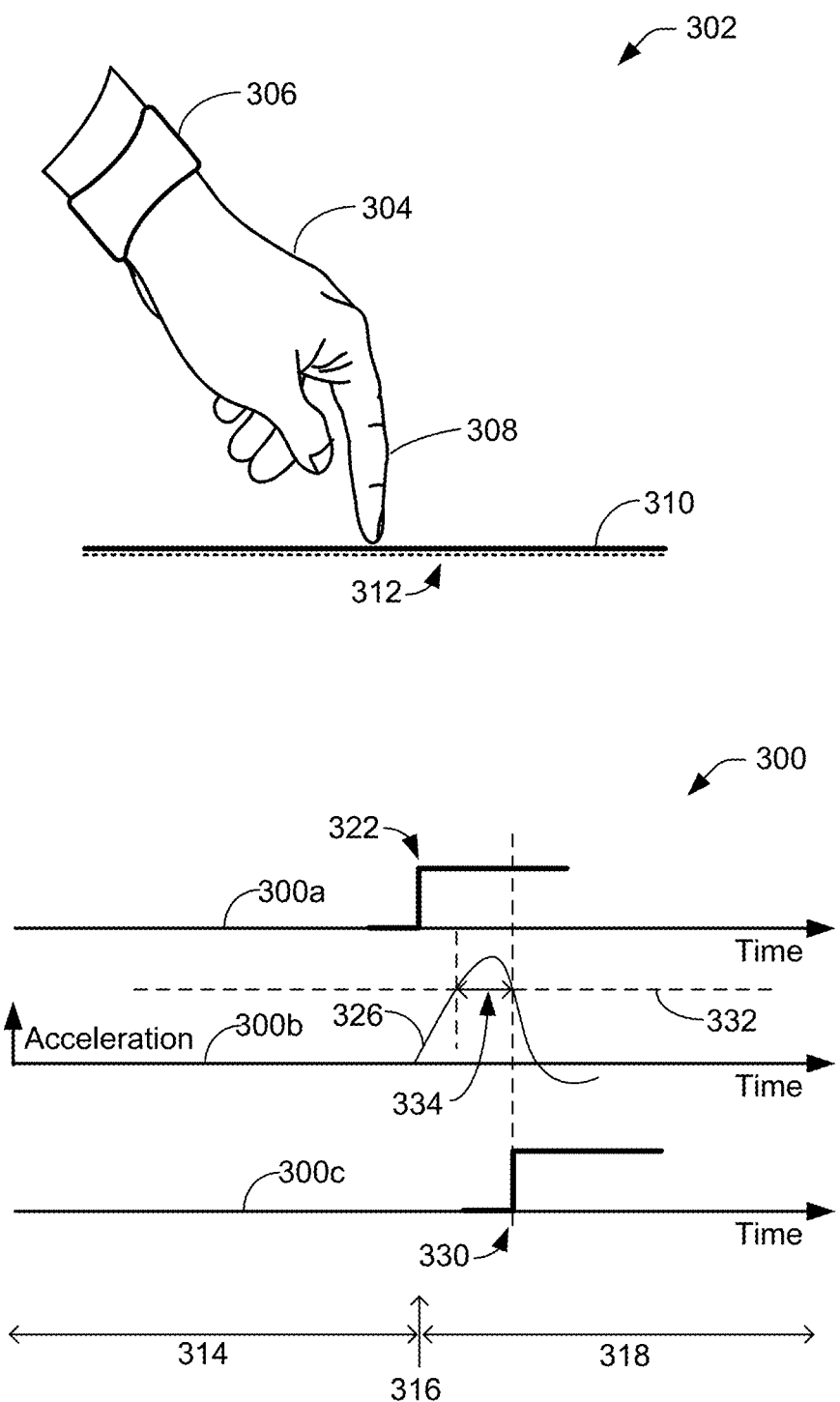
FIG. 3 includes timing diagrams of an example touch event performed by an arm/hand wearing a user-wearable device.

FIG. 3 includes timing diagrams 300 (300*a*, 300*b*, 300*c*) of an example touch event 302 performed by an arm/hand 304 wearing a UWD 306. In this example, touch event 302 comprises a physical contact between a finger 308 and a display surface 310 of a touchscreen 312. In other examples, instead of finger 308, any portion of arm/hand 304, such as more than one finger or a side or back of the hand, may initiate such a touch event by physical contact with display surface 310. Similarly, in some cases the hand touching the display surface 310 might have something in it (e.g., a tucked stylus) which might result in a different motion/acceleration profile/spike that might be recognizable using machine learning and the like (e.g. the spike of a hand or finger(s) touching without the stylus tucked in the hand might be different than a spike of a hand or finger(s) touch with the stylus tucked in the hand).

In detail, touch event 302 involves a time 314 before contact between finger 308 and surface 310, the time 316 at contact, and the time 318 subsequent to the contact. Timing diagram 300a depicts timing of touch event 302 represented by a step 322. For example, a processor (e.g., processor 104 or 210) may operate an application programming interface (API), comprising touchscreen 312, that detects the moment that finger 308 touches surface 310. Timing diagram 300b depicts relative acceleration (hereinafter, the word "relative" need not be explicit and may be implied) of the UWD during touch event 302 and is represented by curve 326. Timing diagram 300c depicts timing of a threshold event, explained below, represented by a step 330.

Before contact, finger 308 (or any portion of an arm/hand) approaches surface 310 with a particular speed or velocity (e.g., speed is a scalar quantity that is independent of direction whereas velocity is a vector quantity that includes magnitude and direction in each of three orthogonal directions) and impinges onto surface 310. UWD 306 generally follows the motion of finger 308. For example, the speed of UWD 306 and finger 308 may be similar or the same, and the path of UWD 306 and finger 308 may be the same but offset by a fixed amount (e.g., a distance between fingertip and the UWD). At the time of contact with surface 310, finger 308 decelerates. In other words, the surface stops the motion of the finger. Hereinafter, deceleration, being a negative acceleration, is referred to as merely "acceleration," unless otherwise described. The motion of UWD 306 corresponds to the motion of finger 308, and thus UWD 306 experiences similar acceleration. In a very small time frame (in one instance between 50 ms to 100 ms), the acceleration increases to a peak value and then decreases, following a profile of a curve, such as curve 326, which is the acceleration profile of UWD 306, and may be described as a pulse. Subsequent to the impact of the finger onto the surface, a small recoil (e.g., bounce) may occur, giving rise to a reverse acceleration, which is illustrated by the portion of curve 326 that is below the time axis. UWD 306, whether worn on an upper arm, wrist, or finger (or other portion of the user), may experience an acceleration profile such as 326.

In some implementations, a UWD may be able to detect the presence of a touch surface, either by a proximity signal or possibly through capacitive coupling (for example). Such detection may subsequently wake up a sensing module to collect a burst of high-bandwidth sensor data. In other implementations, a UWD may be able to initiate high frequency sampling when detection of a relatively large (e.g., "hard") acceleration interrupts the processor of the UWD. Such implementations may be useful for power savings of small battery operated devices, for example. In yet another implementation, the UWD can learn how the user is touching the surface to predict and wake up the system at an appropriate time.

In some cases, finger 308 (or any portion of an arm/hand) may approach surface 310 with a particular acceleration (e.g., a scalar or vector quantity). In examples described herein, however, such an "initial" acceleration may be negligible or ignored in a particular inertial reference frame, so that any initial acceleration is assumed to be zero.

Curve 326 may be described as a pulse having a particular shape that is based, at least in part, on the speed and direction of finger 308 as it approaches and impinges on surface 310. Pulse shape may also depend, among other things, on what portion of a user's arm/hand impinges on the surface, whether a dominant or non-dominant hand performs the touch, where on the user the UWD is worn, extension (e.g., elbow bend) of the user's arm, the size of the user and other physical characteristic of the user, and habits or tendencies that may be particular to a specific user, as described below. For example, the speed and direction of a finger on a dominant hand may be different from that of a finger on a non-dominant hand, and such a difference may lead to different pulse shapes.

In some examples, a technique for determining whether a dominant hand or a non-dominant hand of a user produced a touch event involves establishing a detection threshold (DT), which may be based on experimental and/or statistical data, for instance. A DT is a particular value of acceleration that, when exceeded by a portion of an acceleration pulse of a touch event, indicates some condition that is different from the case where the DT is not exceeded by an acceleration pulse. For example, FIG. 3 illustrates a DT 332 that is surpassed by a peak portion of curve 326. This may indicate that UWD 306 is worn on the same arm/hand as that of finger 308, which performed touch event 302. If curve 326 had a relatively small peak magnitude, as detailed below in FIG. 5, the DT 332 would not be surpassed and it may be determined that the UWD is worn on a part of the user other than the same arm/hand as that of finger 308.

In some examples, a processor may determine that curve 326 produces a touch event subsequent to when curve 326 rises above DT 332. In particular, when curve 326 subsequently falls below DT 332, the processor determines that touch event 302 has occurred, as represented by a step 330. In some implementations, the processor may consider a time limit measured from when touch event 302 occurs, e.g., step 322. If, for example, an acceleration pulse (e.g., represented by curve 326) fails to exceed DT 332 within such a time limit, then the processor may determine that the acceleration pulse was initiated by an arm/hand opposite to that which is wearing the UWD. In some examples, such a failure of an acceleration pulse to exceed DT 332 within such a time limit may be indicative of a case where the acceleration pulse is negligible and is merely noise and is not caused by a touch event.

The shape of an acceleration pulse may indicate a number of things, described below. For example, an acceleration pulse may include a particular shape or feature(s) that allows system 200 to determine that a particular user produced the acceleration pulse. In other words, a particular user may produce a distinct and identifiable acceleration pulse caused by particular movement habits or tendencies. The shape of an acceleration pulse may be characterized by, among other things, slope at various parts of the pulse, peak magnitude, full-width-at-half-max (FWHM), and pulse a width 334 at a DT, such as 332. Claimed subject matter is not limited to such examples, of course, and any of a number of other approaches may be used to detect pulses, including approaches involving machine learning.

Figure 4:
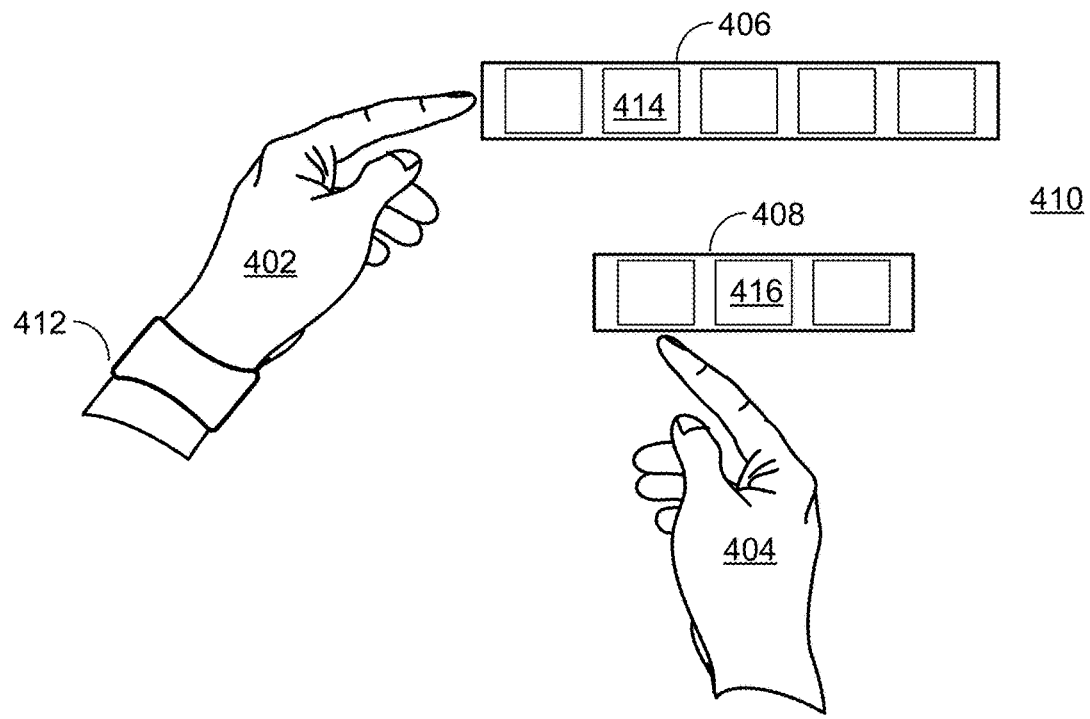
FIG. 4 depicts arms/hands of a user interacting with exemplary objects displayed on a touchscreen.

FIG. 4 illustrates arms/hands 402 and 404 of a user interacting with example objects 406 and 408 displayed on a touchscreen 410. In some examples, a UWD may be worn on a dominant arm/hand, and in other examples, a UWD may be worn on a non-dominant arm/hand. In the example illustrated in FIG. 4, arm/hand 402 is considered to be the dominant arm/hand and is wearing a UWD 412. Arm/hand 404 is considered to be the non-dominant arm/hand and is not wearing a UWD.

Objects 406 and 408 may comprise any of a number of displayable things, such as windows, menus, text, drawings, icons, images, and so on. For example, if object 406 is a menu, then object 414 may be one of a number of menu items that may be selected by the user touching object 414. In some examples, object 408 may comprise text that includes a number of words 416, which may be selected by the user touching any of the words.

As discussed above, when interacting with an object or device, each hand of the user may have a different role. For example, non-dominant hand 404 may be specialized to position object 408 for dominant hand 402. In some configurations, a system may automatically distinguish a dominant hand versus a non-dominant hand of a user by receiving wireless signals transmitted from UWD 412 to the system which are representative of motion of the UWD. Motion of the UWD may correspond to motion of hand 402 and 404 (though the motion correspondence between hand 402 and UWD 412 may be closer than that between hand 404 and UWD 412). It should be noted that either the right hand or the left hand could be the dominant hand of a user.

Figure 5:
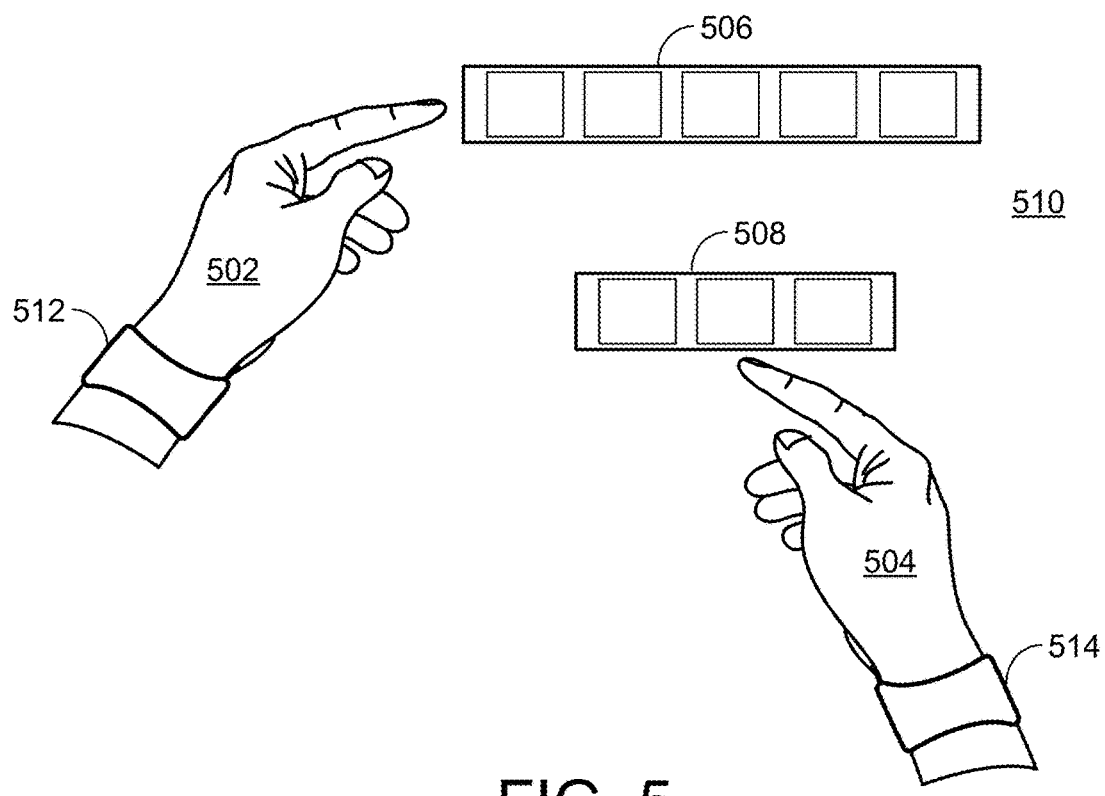
FIG. 5 depicts arms/hands of two users interacting with objects displayed on a touchscreen.

FIG. 5 illustrates arms/hands 502 and 504 of two different users interacting with example objects 506 and 508 displayed on a touchscreen 510. In some examples, a UWD 512 may be worn on a (dominant or non-dominant) arm/hand of a first user, and a UWD 514 may be worn on a (dominant or non-dominant) arm/hand of a second user. Objects 506 and 508 may comprise any of a number of displayable things, such as windows, menus, text, drawings, icons, images, and so on.

In some implementations, a system may determine which user, among the two users, is performing a touch event with the touchscreen. For example, UWDs 512 and 514 may provide identification data for their respective wearers to the system. The system may correlate touch events (e.g., timing thereof) with motion of the UWDs and the identification data they provide. For example, UWD 512 may provide such identification data to the system periodically, from time to time, in response to a request from the system, or at the time of a touch event. If the system senses of a touch event (e.g., via electronics of the touchscreen), the system may correlate this touch event with motion of UWD 512 and motion of UWD 514 to determine which user initiated the touch event. The correlation between the touch event and the motion of the UWD worn on the arm/hand that initiated the touch event will be stronger than the correlation between the touch event and the motion of the UWD worn on the arm/hand that did not initiated the touch event. Accordingly, the system may determine which user initiated the touch event. Though this example involved two users, such an approach may be performed by a system for any number of users interacting with a touchscreen, for example.

1.5 Multi-Touch Detection Implementations

The above-described exemplary operating environment 100 and exemplary system 200 can be used to enable various multi-touch detection implementations as described herein. The following multi-touch detection implementations provide various tools for improving the usability of a display device, such as for example, a large touchscreen device. These tools include, among others, user-associated personalized mobile menus, combined click-through and radial marking menus, menus to automate and improve drawing or manipulation of content on a display, new menus and methods of selecting objects and text on a display, and new interactions with UWDs and touchscreen displays by using UWDs with gestures. In addition, targeted haptic feedback to the UWD of specific users of a display is enabled. Haptic feedback in the form of vibration can be provided to the UWD of a specific user for example, in one instance, when he/she snaps an object to a grid.

Some multi-touch detection implementations described herein utilize a UWD as described above in conjunction with a display to allow new and advantageous interfaces with a touch screen display, either large or small. In many multi-touch detection implementations a user's dominant and non-dominant hand are determined using the UWD as described herein (and/or via other method such as by determining fingerprints of a user and/or by using cameras to track the user). This allows the determination of when the user's non-dominant hand (or dominant hand) touches the touch screen display as discussed in the paragraphs above. In some multi-touch detection implementations a user's non-dominant hand wears the UWD (e.g., a band) and uses an accelerometer and/or one or more other sensors on the UWD to determine when the user's non-dominant hand makes contact or touches the touch screen display. In other multi-touch detection implementations a user's dominant hand wears the UWD (e.g., a band) and uses an accelerometer and/or one or more other sensors on the UWD to determine when the user's dominant hand makes contact or touches the touch screen display. Or in some implementations, sensors on a device being held or touched, or sensors on a UWD, or a combination of both, can be used to determine which hand is dominant and non-dominant and which hand is touching or otherwise acting on the touch screen display.

1.5.1 Mobile Personalized Menus

Many multi-touch detection implementations described herein provide menus that move with the user's finger touching the display (in some implementations as long as the same touch event is present) This is advantageous, for example, in that a user can freely move about a large display without having to reach for menus in order to add or manipulate objects or data. In some implementations when a finger, or more than one finger, of a user's (e.g., non-dominant) hand is determined to touch the touchscreen, a menu is displayed on the display at the location of the finger(s) on the display. In some implementations, this menu follows the finger of the (non-dominant) hand of the user throughout the display as long as the finger is touching the display. In some multi-touch detection implementations, if the user lifts this finger of the (non-dominant) hand from the display (e.g., the touch event is no longer present) the menu disappears from the display. In some implementations the user's non-dominant hand can be used to activate various options on the menu (e.g., using a finger on the non-dominant hand), or the user can add objects or strokes with the pen in their dominant hand or with a finger of their dominant hand. It should be noted that the roles of the dominant hand and the non-dominant hand in menu display and manipulation can be reversed.

In some multi-touch detection implementations described herein, personalized menus can be displayed to each user when that user touches the display. For example, the user's identity can be determined using the UWD as described previously and this determined identity can be used to associate personalized menus and personal data to the specific user. As a result, two or more different users can simultaneously manipulate data (e.g., files, images, search results) and objects on a large display, each using their own personalized data and personalized menus (e.g., menus the user most often uses, menus configured to conform with the user's preferences, such as, for example, preferred shape of a French curve, preferred dictionary for handwriting recognition, automatically selected latest color and/or property of a pen if pen unique ID is associated with a specific user, and so forth). Also, in some implementations, the personalized menus and preferences can seamlessly follow the user across different devices (i.e., by storing/retrieving this information via a computing cloud). In one instance, this could be implemented by having the UWD communicating credential and/or user information to the computing device/processor connected to the display (or remotely connected to the display) and use this information automatically and securely to retrieve data from a computing cloud (i.e., using a Web service and the like). Then the data can be displayed in proximity to the user. The personalized menus can also be mobile so that they move with a touch event as described above, or can be non-mobile so that they do not move.

1.5.2 Combined Click-Through Radial Marking Menus

Some multi-touch detection implementations described herein use combined click-through radial marking menus. These combined click-through marking menus can be used as normal radial marking menus but can also allow the combined click-through radial marking menu to be positioned over an object that a user wishes to act on displayed on a touchscreen by touching the touchscreen or gesturing (e.g., with a finger of the user's non-dominant hand) which then displays a radial marking menu icon. The user can then expand the radial marking menu and select a menu option from the radial marking menu by touching the menu icon (e.g., with their dominant hand or a pen) in an outward motion from the center of the radial marking menu over the desired menu choice. The user can thus modify the object underlying the combined click-through radial marking menu using the selected menu option. For example, the user can modify the stroke color or stroke width of a line underlying the menu. In some implementations the combined click-through radial marking menu can be expanded from an unexpanded state (represented by an icon) by applying a certain degree of pressure to the touch display. In other implementations, the user may twist their non-dominant hand (which can be sensed by the UWD) to expand the menu. In some implementations, the combined click-through radial marking menu modifies the color of the stroke(s) just below the menu and the radial marking menu selection modifies the state of the pen which is persistent (e.g., color of that specific pen which can be determined in various manners). Of course, many other stroke attributes could also be modified, such as stroke thickness, stroke style (e.g., semi-transparent highlighter, marker, dotted lines, air spray, etc.) For example, if the state of the pen is green (e.g., the latest radial menu selection is green) and the user clicks through to modify existing strokes to red, the state of the pen stylus remains as green (until the next different radial menu selection). In some implementations, the click-through behavior or a menu is recognizable visually by the menu being semi-transparent on the display.

Figure 6:
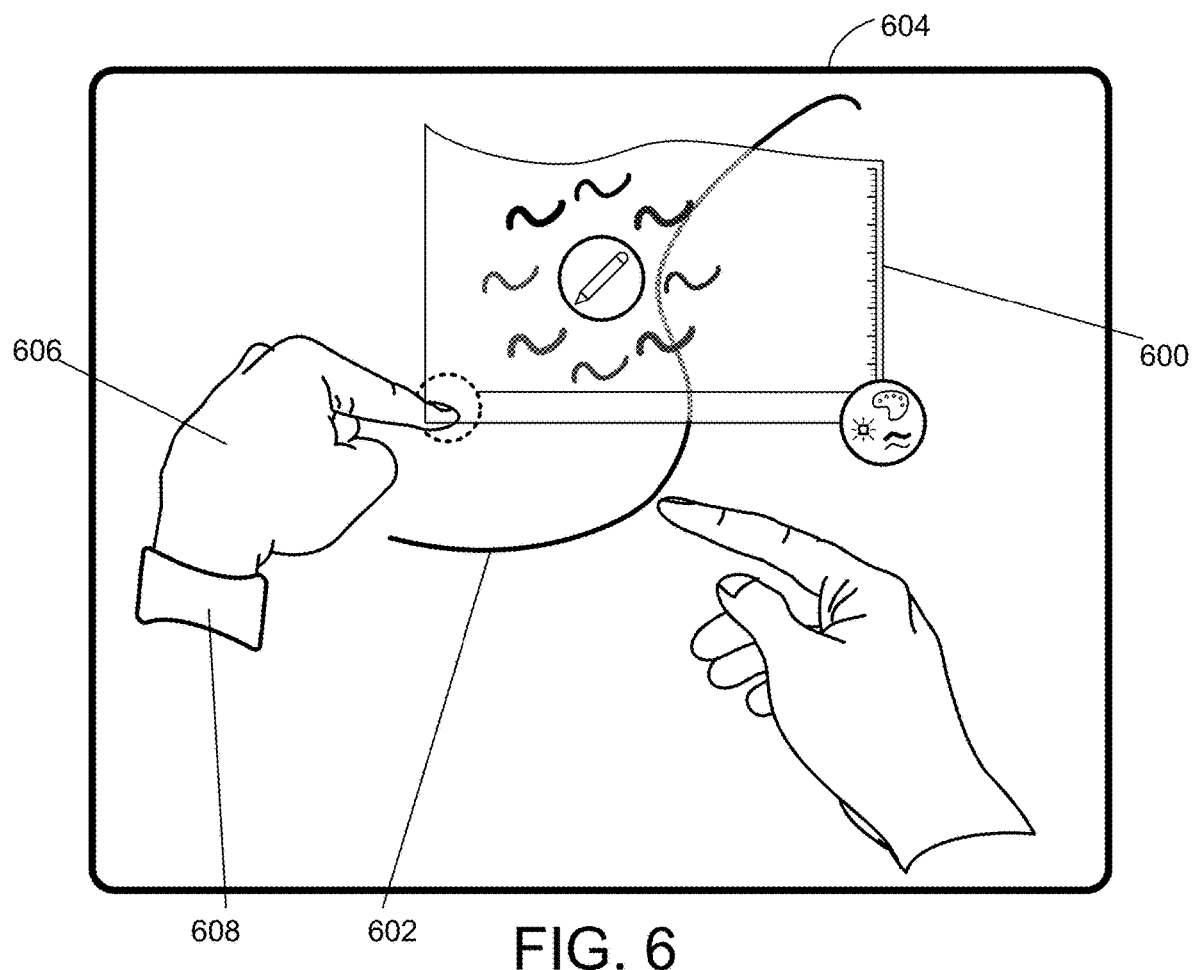
FIG. 6 depicts an exemplary combined click-through and radial marking menu that is used to modify stroke characteristics of a stroke drawn on a touch screen display.

FIG. 6 depicts an exemplary combined click-through and radial marking menu 600 that is used to modify stroke characteristics (for example, the width) of a stroke 602 drawn on a touchscreen display 604. In some implementations the menu 600 appears on the display 604 when a user touches the display 600 with their non-dominant hand (which can be referred to as a non-dominant touch) as determined by a UWD 608. The user can then modify the stroke 402 by selecting a menu item with the user's dominant hand (which can be referred to as a dominant touch).

Figure 7:
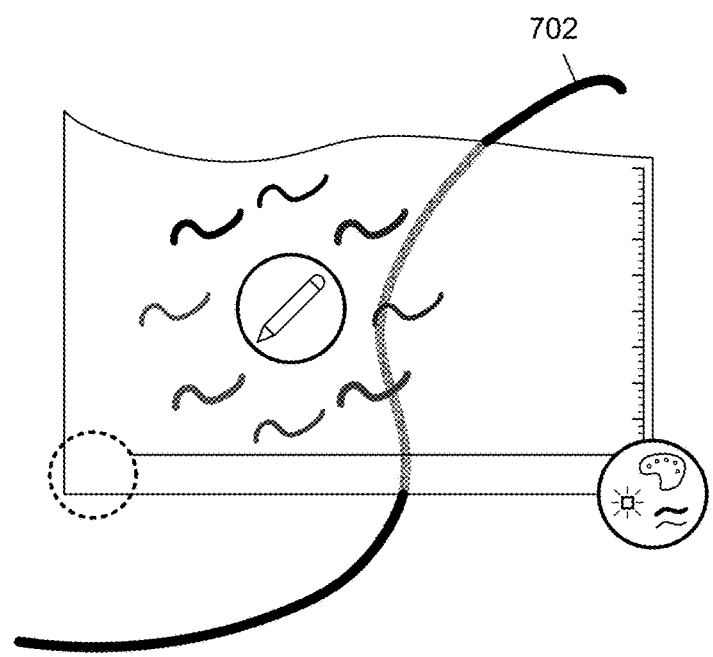
FIG. 7 depicts the modified stroke characteristics of the stroke drawn on the touch screen display depicted in FIG. 6.

FIG. 7 depicts the modified stroke 702 characteristics of the stroke drawn on the touch screen display depicted in FIG. 6 (e.g., the stroke is thicker). It should be noted that this example assumes that the user's non-dominant hand is the left hand, but a symmetrical menu could appear if the non-dominant hand was the right hand (in one implementation, the UWD can inform the display/processor of the computing device of the handedness).

1.5.3 Content/Object Selection and Manipulation Using X-ray Menus

Some multi-touch detection implementations provide for the selection of content or objects on a screen and action thereon using x-ray menus. In general, an x-ray menu integrates the selection of scope (e.g., which stroke(s) or other objects to recognize, or otherwise act upon) with the articulation of a command itself. When compared to other methods of selection of items on a display, such as switching to a lasso mode, and then delineating the strokes/objects to be selected with a lengthy pen stroke, x-ray menus require much less user interaction and therefore are computational efficient. In some implementations X-ray menus allow desired content to be selected by selecting the objects or content in an area defined by a number of digits on a user's (e.g., non-dominant) hand (for example, two fingers or a finger and a thumb of the non-dominant hand of a user). One or more menus that allow manipulation of the selected objects or content on the display associated with the selected content/object can appear at the edges (or at other locations such, as for example, next to the selected content, close to the non-dominant finger, at the top or bottom of the selection, etc.) of the selected content or objects. In some implementations, the selected area gradually fades further away from the intersection of the digits/fingers of the user making the selection. Furthermore, in some implementations the distance the selected region extends from the digits/fingers can be increased by increasing the pressure of the digits/fingers touching the touchscreen apply to the touchscreen. In some implementations, the selected region extends when the user performs some kind of gesture with a finger or pen (e.g., an outward movement of the dominant hand on the x-ray to extend it, and inward movement to retract it). Additionally, the selection of content or objects can be redirected by the repositioning of the digits/fingers that are touching the screen.

Figure 8:
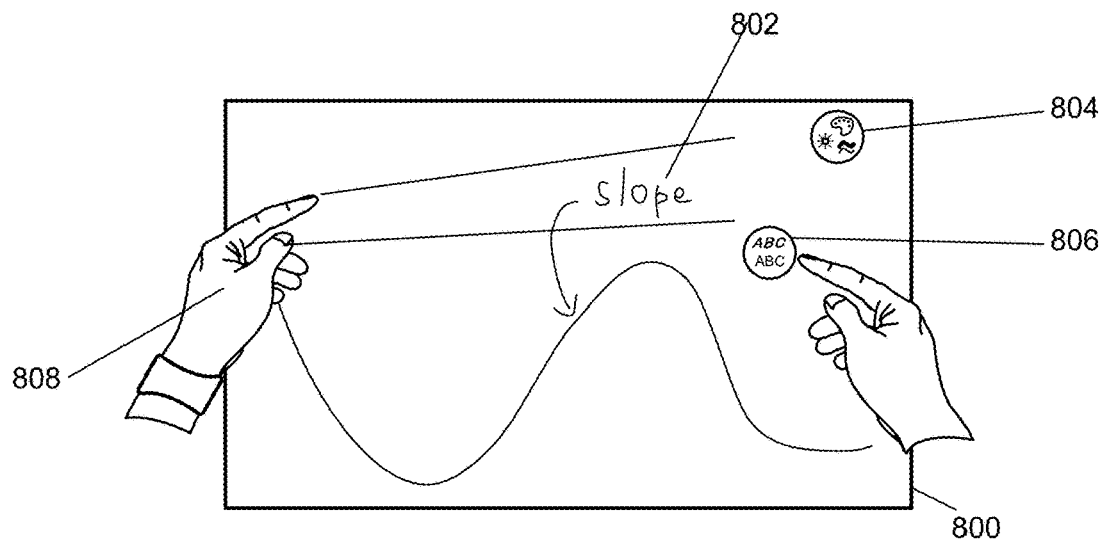
FIG. 8 depicts the selection of content on a touchscreen using two fingers or a finger and a thumb with associated displayed menus, herein called an x-ray menu. The selection of the content can be redirected by repositioning, resizing or rotating the two fingers (or finger and thumb) or some other predefined number of fingers/thumbs. One or more other body parts, pen(s) and/or other object(s) can also be used to create the x-ray menu. This example shows selection of the handwritten text 'slope' and the display of associated menus for the application of text recognition to the handwritten text.

FIG. 8 depicts the selection of an area of display that contains content (e.g., the word 'slope') on a touchscreen 800, including unexpanded menus 804, 806 that are associated with the selected area. In other implementations, the locations of these menus could be different. In some implementations, this selected area and associated displays are initiated by touching the display 800 with the digits of a user's non-dominant hand. This example shows selection of the handwritten text 'slope' and the display of associated menus for the application of text recognition to the handwritten text.

Figure 9:
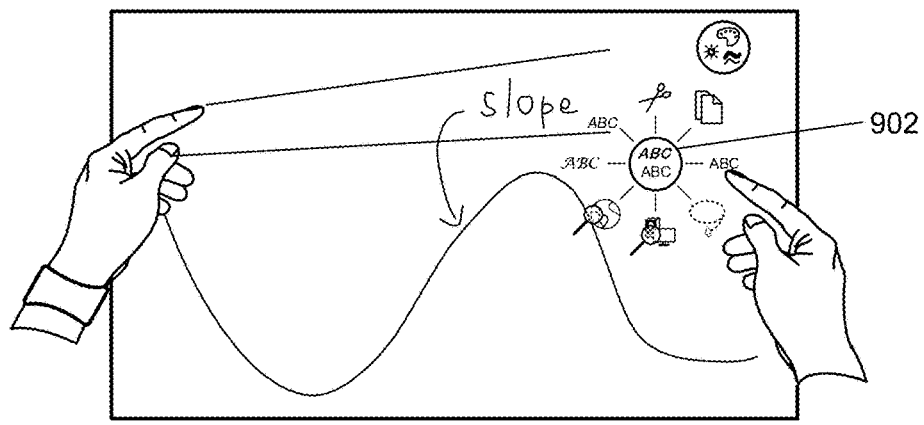
FIG. 9 depicts the expansion of the text recognition menu shown in FIG. 8. The menu 902 could also be selected with a stylus (or other object) instead of a finger.
Figure 10:
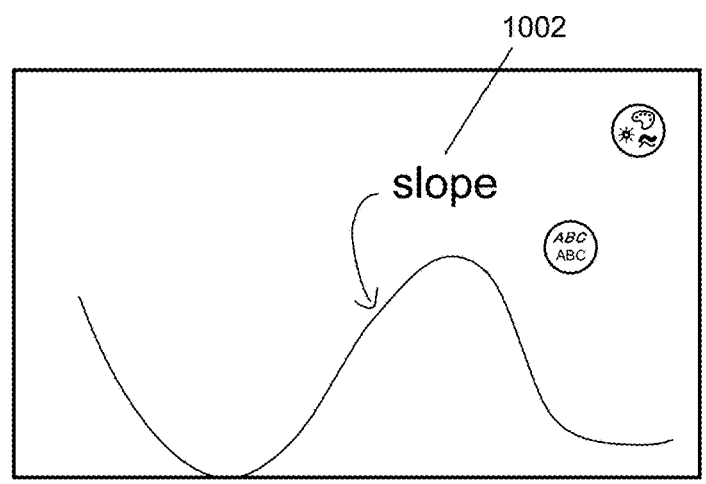
FIG. 10 depicts the handwritten text 'slope' converted to type written 'slope' after application of text recognition being activated with the combined click-through radial marking menu shown in FIGS. 8 and 9. In some implementations, once the fingers are removed from the display, the X-ray menu is removed and the radial marking menus are not visible either.

FIG. 9 depicts the expansion of a combined click-through and radial text recognition menu 902 shown in FIG. 8. In some implementations, this menu can be expanded by a user pressing and holding down the center of the menu with a finger or stylus/pen. FIG. 10 depicts the handwritten text 'slope' converted to type written 'slope' 1002 after application of text recognition being activated with the combined click-through radial marking menu shown in FIGS. 8 and 9. In some implementations, there is an 'unrecognize' menu that allows reverting the recognition. It should be noted in this example that if the text were not horizontally oriented, the orientation of the user's two digits/fingers that define the orientation of the x-ray could also be used to correctly orient the selection of text to be recognized. In one instance, the recognized text could keep the same orientation (and size, and other characteristics such as bold if thick strokes, color, italic, etc.) as the handwritten text.

There are also various other ways that a user can select content in various multi-touch input detection implementations described herein. In some multi-touch detection implementations, the area selected for editing or modification of objects is not defined by the area between two fingers of the (e.g., non-dominant) hand of the user but is instead defined by a fixed distance from the touch of a finger of the (e.g., non-dominant) hand. For example, an area of a radius of a given distance around the location of the touch of the user's finger can be used to select objects and content displayed on the display. Applicable menus to manipulate the selected content can also be displayed (for example at the boundaries of the radius of the circle defining the selected content).

1.5.4 Menu Contour as a Tool

In some multi-touch detection implementations the menu contours are an implicit part of the tool palette/menu itself that allow a user to use a pen to sketch out curves or straight lines by making a pen stroke in reasonably close proximity (e.g., within a specified distance) of the menu/tool palette itself conform to the shape of the contour of the menu/tool palette. The shape of the line is not provided by a separate mode, or tool, that is selectable from the palette per se; rather it exists only tacitly, in effect as a spatially-multiplexed function which the user accesses simply by making a pen-stroke in reasonably close proximity to the appropriate border of the tool palette. This is different from previous French curves, curve guides, and straightedge tools where the tool always first exists as some sort of control that has to be selected from within the palette (or toolbar, or wherever the function resides in a graphical user interface). This design sidesteps that and the menu/tool palette itself embodies that behavior merely based upon the outer contours of the menu/tool palette as a whole.

Figure 11:
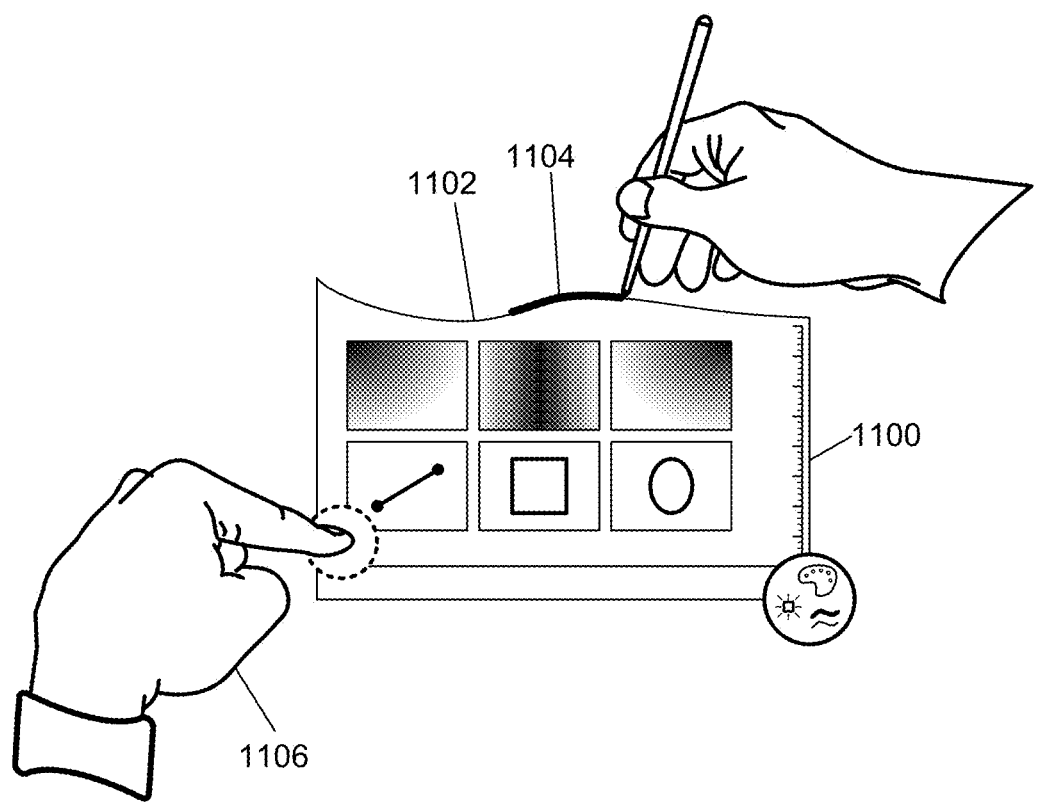
FIG. 11 depicts a menu whose contours can be used as a drawing tool, such as a French curve, a straight edge, a circle or other shape which can be used to assist a user in drawing. The contours of the menu can be changed by a user and can also be used to perform other tasks besides drawing (e.g., cutting or masking content on the display) without having to activate specialized controls for these purposes.

FIG. 11 depicts a menu 1100 with a contour 1102 that acts as a tool to draw a French curve or other shape. The contour 1102 of the menu 1100 can be used as a tool without having to bring up a specific drawing tool menu or control. FIG. 11 depicts a user drawing a curve 1104 that conforms to the contour 1102 of the menu 1100 by merely drawing a stroke in vicinity of the contour of the menu. In one implementation the menu is activated by a finger of the user's (e.g., non-dominant) hand 1106 touching the display. In some implementations the orientation of the whole menu 1100 can be rotated by the user, but in some cases the radial menus (that are within the menu 1100) keep their orientation (e.g., with the North menu selection remaining pointed upward). In other instances, the radial menus are rotated with the menu 1100 (so the North marking on the radial menu is in the Northwest (NW) direction when the menu 1100 is rotated).

Figure 12:
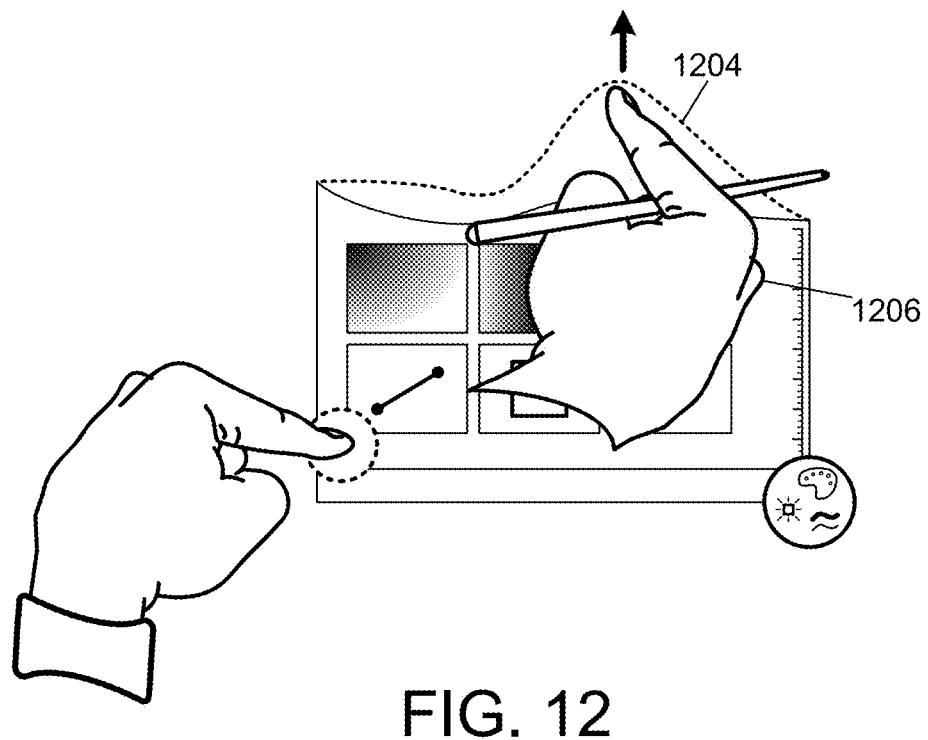
FIG. 12 depicts the modification of a curve drawn in FIG. 11 where a user modifies the curve by using touch or multi-touch (i.e. with the user's dominant hand) to modify the characteristics of the contour of the menu.

FIG. 12 depicts a curve 1204 that represents the modification of the curve 1104 drawn in FIG. 11. The user modifies the curve 1004 by using touch or multi-touch (i.e., with the user's dominant hand) to modify the characteristics of the curve. In some implementations the user can change the shape of the curve to be drawn by changing the contours of the menu itself. In this case any stroke drawn within a specified distance of the modified menu contour will conform to the new modified menu shape. These modifications could be personalized for the user making them and can follow the user when the user is using a different device. Also, in one instance, the history of the modifications of the French curve tool can be stored or different custom French curve tools can be set by the user as different preferences for shortcut menus, etc.

In some multi-touch detection implementations, the contours of the displayed mobile menus are used as other types of tools. For example, in some implementations the contours of the menu are used as a straightedge or a ruler. Furthermore, in some implementations the edge of the menu can be used as an alignment tool, e.g., as a border to drag objects against. Alternately, or in addition, the menu contour can be used as a frisket (mask). The menu contour can also be used to enforce particular kinds of constraints or symmetry, such as, for example, mirror-image reflection of the current pen stroke. In some multi-touch detection implementations the menu contours can be used to snap a straightedge to 90-degree or 45-degree increments by default. Furthermore, a modified gesture can be used to allow a user to break the constraint and place the straightedge at an arbitrary angle. In some multi-touch detection implementations, the menu contours can be used to provide a compass or protractor edges. In another example, an edge could apply a line style, etc. (i.e., a dotted line, a line with grid ticks and so forth). These implementations are advantageous in that they make user input simpler and more computationally efficient and the user never feels like they have to "select" or use a tool mode—they are still just laying down strokes with a pen in what feels like a completely modeless fashion—yet added functionality is ever-present and can be accessed in a seamless manner when they need it.

1.5.5 Gestures Combined with UWD for Menu Control

In some multi-touch detection implementations, gestures are used to control the menus displayed. For example, in some of the multi-touch detection implementations discussed previously when a user touches a touch display with a finger of his or her non-dominant hand, a menu pops up at the location of the finger touch. In some implementations, this menu typically disappears when the user is no longer touching the display. In some multi-touch detection implementations, however, a user can gesture in a predefined manner in order to manipulate the menu on the display. For example, in some multi-touch detection implementations a user can lock a displayed menu into place on the display by twisting the finger, hand or arm of the non-dominant finger that is touching the display and that pops up the menu on the display. In some implementations, a visual feedback (e.g., change in color, change in transparency) is provided to indicate that the menu has been locked. The user's finger twisting can be determined by accelerometers and/or one or more other sensors on a UWD the user is wearing. In this case the displayed menu is locked into position on the display and remains displayed until the user chooses to move the menu or close it, for example by touching the menu again with the finger of the non-dominant hand and then removing their finger from the display (e.g., without twisting). Other gestures can be used to execute other commands on the menu. For example, a user can raise their hand in a certain gesture to make the menu disappear, expand menus and make menu selections.

1.5.6 User Specific Haptic Feedback Combined with UWD

In some multi-touch detection implementations a user cannot only receive data from the UWD, but commands can also be sent to the UWD to execute mechanical actions by the UWD. In some implementations, the UWD includes a sound and/or vibration generating device that may alert the user (and/or other users) if a user's arm/hand has taken a specific action to particular objects on the display. For example, in some implementations a user can be sent haptic feedback for actions the user takes with respect to the display. For example, the user can receive haptic feedback on their UWD when the user changes menus, selects a specific menu, snaps a stroke or strokes to a menu contour, snaps an object (or a group of objects) to a grid, or takes other actions on objects or menus displayed on a display. In another implementation, a first user may snap an object and receive haptic feedback, but other users touching the display (and/or in proximity to it) will receive a different feedback (i.e., a notification at the same time) or no haptic feedback at all. In yet another instance, a user touching the display will receive a different feedback than other users that are in proximity of the display (e.g., within a prescribed distance from it) but are not touching it. In yet another instance, the actual distance from the users to the display affects the type and/or intensity, and/or frequency, etc., of the haptic feedback (i.e., very small haptic feedback is provided if the user is far away from the display).

Since the user's identification is known because it is associated with his UWD, this haptic feedback can be personalized based only on the actions this specific user takes. It should be noted that this haptic feedback or audible alert sent to the UWD can be concurrent with a touch event on a touch screen but can also come after or before such a touch event, or may not be related to a touch event at all. In some implementations, a user performing an operation will not receive haptic feedback but other users may receive haptic feedback. In some cases, the haptic feedback is sent during an operation with the hand that is not wearing the UWD. Haptic feedback can also, in some implementations, be related to a hover event (e.g., hovering with a stylus over a grid).

1.5.7 Portability to, and Distributed Processing with, Smaller Screens

In some multi-touch detection implementations menus and tools described herein displayed on a large touch display can either partially or totally be ported to a smaller display or another device such as mobile phone or a hand held tablet device (or vise versa). For example, in these exemplary implementations menus and tools displayed on a large screen device can be ported over to a hand held device. Many of the same interactions that are discussed herein can be supported in such a context which allows a user (for example) to take advantage of some of the capabilities of the multi-touch detection implementations described herein even when the user is somewhat beyond arms-length of the display. In some implementations, entire menus or portions thereof can be marshaled off to a display of a UWD, and/or a mobile phone, and/or some other wearable and/or non-wearable mobile device (e.g., tablets, watches, or possibly even to a pen itself). In one implementation, the system knows which user touches the display because of the UWD, so this information allows connection to devices such as tablets, mobile phones, or pens associated with that user and marshals menus or portion of menus to them. For example, if the device is a pen, user preferences can automatically be set (i.e., style of the stroke, color, size of the stroke, etc.) In some implementations a touch-sensitive device such as, for example, a touch pad on a computing device can be used by a non-dominant hand of a user and a mouse can be used by the dominant hand of the user to control a non-touch display or touch display such as, for example, a large display in a conference room. Furthermore, a correlation between the movement of the mouse (or touch events on the touchpad) and a movement of a UWD associated with the user can be used to seamlessly authenticate the user.

Figures 13, 14:
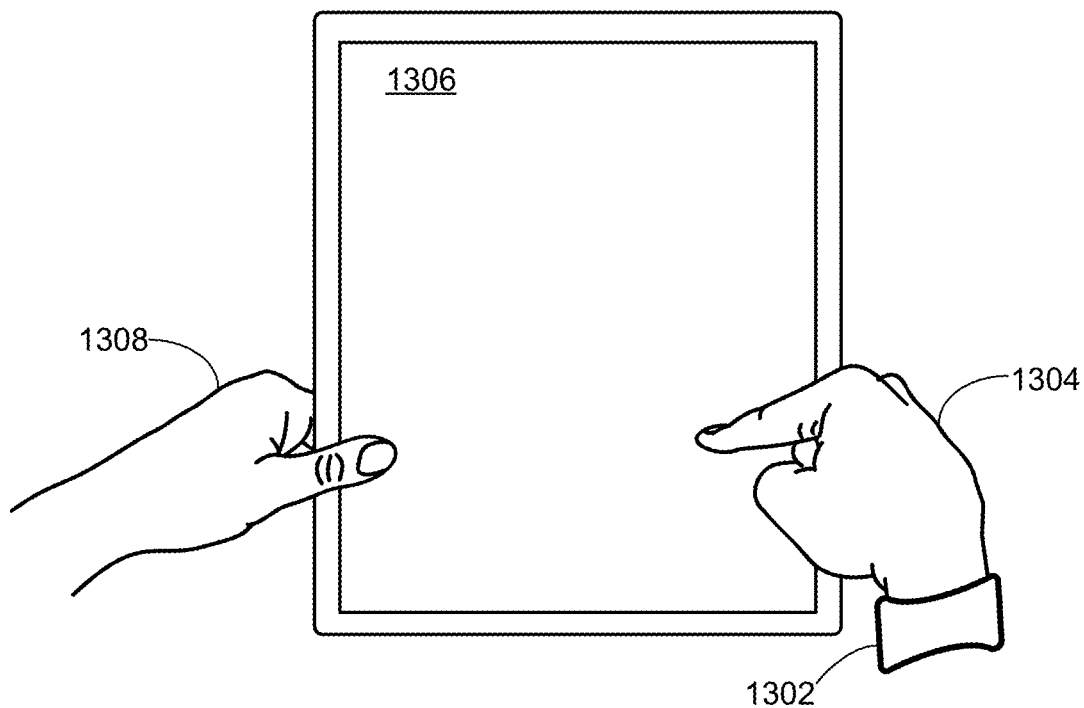
FIG. 13 depicts a user using a hand held computing device with a small screen to implement multi-touch detection implementations as described herein.
FIG. 14 depicts an exemplary computer-implemented process which can be used to practice various multi-touch detection implementations as described herein.

FIG. 13 illustrates a UWD 1302 worn by a user on arm/hand 1304, which is interacting with a handheld touchscreen 1306 which can be used to port some of the tools and menus described herein to another device for display. For example, a user's personalized menus can be ported to other display devices of the same size or can be ported between large and small screen displays. In general, menus can be spread across all devices of a user regardless of their shape, sensing capabilities and size. Also, in one implementation (for example, on a tabletop display) a system can recognize when a user puts a mobile device (e.g., mobile phone) down on the display (i.e., by determining a specific spike in the accelerometer and/or gyro on the device and footprint of the mobile device on the display) and automatically create a mixed experience such as having a customized French curve for that user appearing around the mobile device on the tabletop display, and having other menus displayed on the mobile device itself.

1.5.8 Exemplary Process

FIG. 14 is a flow diagram of an exemplary computer-implemented process 1400 that may be performed by a processor. For example, process 1400 may be performed by computing device 102, illustrated in FIG. 1.

At block 1402, the processor receives a touch event on a touch display in communication with the computing device from a user.

At block 1404, as long as the touch event is active, a tool is displayed on the touch display at the location of the touch event, wherein the tool provides capabilities for modifying an object displayed in a specified vicinity of the touch event on the touch display. The tool can be fixed to the display even when the touch event ends in response to a user gesture.

The flow of operations illustrated in FIG. 14 is illustrated as a collection of blocks and/or arrows representing sequences of operations that can be implemented in hardware, software, firmware, or a combination thereof. The order in which the blocks are described is not intended to be construed as a limitation, and any number of the described operations can be combined in any order to implement one or more methods, or alternate methods. Additionally, individual operations may be omitted from the flow of operations without departing from the spirit and scope of the subject matter described herein. In the context of software, the blocks represent computer-readable instructions that, when executed by one or more processors, configure the processor to perform the recited operations. In the context of hardware, the blocks may represent one or more circuits (e.g., FPGAs, application specific integrated circuits—ASICs, etc.) configured to execute the recited operations.

Any routine descriptions, elements, or blocks in the flows of operations illustrated in FIG. 14 may represent modules, segments, or portions of code that include one or more executable instructions for implementing specific logical functions or elements in the routine.

2.0 Example Clauses

The following paragraphs describe various multi-touch detection implementations.

A. A system comprising: a touchscreen; one or more processors; a transceiver to receive signals from a device associated with a user and to send signals to the device associated with the user; and a memory storing instructions that, when executed by the one or more processors, cause the one or more processors to perform operations comprising: receiving data representative of acceleration of a sensor resident in the device associated with the user during a touch event of the touchscreen; determining, based at least in part on the received data, if the touch event is associated with a dominant input or if the touch event is associated with a non-dominant input; initiating a first command if the touch event is associated with a non-dominant input; and initiating a second command if the touch event is associated with a dominant input.

B. The system as paragraph A recites, wherein the stored instructions, when executed by the one or more processors, cause the one or more processors to perform operations comprising: displaying at least one menu at the location of the touch event on the touchscreen in response to the first command.

C. The system as paragraph B recites, further comprising using the second command to modify at least one object displayed by the touchscreen using the at least one displayed menu.

D. The system as paragraph B recites, wherein the menu moves with the movement of the touch event on the display as long as the touch event remains active because the user or other object is touching the touchscreen.

E. The system as paragraph B recites, wherein the menu is personalized to the user associated with the first touch event.

F. The system as paragraph B recites, wherein the at least one menu further comprises at least one radial marking menu that is also used to modify an object that is underlying the menu on the touchscreen.

G. The system as paragraph B recites, wherein the touch event is determined to be caused by a specified number of digits of the user's hand touching the touchscreen, and wherein objects in an area between the specified digits are selected and modifiable by the menu that is associated with the selected area on the touchscreen.

H. The system as paragraph B recites, wherein the touch event is determined to be caused by a touch event of the user's hand touching the touchscreen, and wherein one or more objects in an area around the touch event are selected and modifiable by a menu that is associated with the selected area on the touchscreen.

I. The system as paragraph B recites, wherein the contours of the boundaries of the menu are used as a tool to act on objects displayed on the touch screen.

J. The system as paragraph I recites, wherein the contours of the boundaries of the menu are modifiable by a user.

K. The system as paragraph A recites, wherein one or more commands to the device associated with the user are wirelessly sent to the device associated with the user via the transceiver.

L. The system as paragraph K recites, wherein the one or more commands are a haptic input.

M. The system as paragraph K recites, wherein the one or more commands are targeted to the device associated with a specific user.

N. The system as paragraph A recites, wherein the dominant input is associated with a dominant hand of a user of the touchscreen and the non-dominant input is associated with a non-dominant hand of the user.

O. The system as paragraph A recites, wherein the stored instructions, when executed by the one or more processors, cause the one or more processors to perform operations comprising: receiving data from the device associated with a user representative of identification of the user of the associated device; and modifying the menu displayed on the touchscreen based, at least in part, on the identification of the user.

P. The system as paragraph A recites, wherein a device associated with a user is a user wearable device.

Q. A system comprising: a first touchscreen; a receiver to receive signals from a user wearable device; a processor communicatively coupled to the receiver to: receive data representative of acceleration or other motion data of the user wearable device during a touch event on the first touchscreen performed by a user; determine, based at least in part on the received data, which hand of the user produced the touch event; and display a tool associated with the user at a location on the touchscreen corresponding to a location of the touch event on of the first touchscreen based, at least in part, on the determination of which hand of the user produced the touch event; and port the displayed tool associated with the user at the location in the first touchscreen to a similar relative location on a second touchscreen.

R. The system that paragraph Q recites, wherein the processor is further communicatively coupled to a memory to: store at least a portion of the acceleration or other motion data and associate the stored acceleration or other motion data with the user; store additional acceleration or other motion data of a second user of the touchscreen and associate the stored additional acceleration or other motion data with the second user; and access the stored acceleration or other motion data and the stored additional acceleration or other motion data to determine whether the user or the second user produced the touch event.

S. The system that paragraph R recites, wherein the processor is configured to modify at least one object displayed by the touchscreen based, at least in part, on the determining whether the user or the second user produced the touch event.

T. A computer-implemented process method comprising using a computing device for: receiving a touch event on a touch display in communication with the computing device from a user; and as long as the touch event is active, displaying a tool on the touch display at an approximate location of the touch event, wherein the tool provides capabilities for modifying an object displayed in a specified vicinity of the touch event on the touch display.

U. The computer-implemented process that paragraph T recites, wherein the tool can be fixed on the touch display even when the touch event ends by using a user gesture.

V. The computer-implemented process that paragraph T recites wherein the tool moves with the location of the touch event as long as the touch event is active.

Although the techniques have been described in language specific to structural features and/or methodological acts, it is to be understood that the appended claims are not necessarily limited to the features or acts described. Rather, the features and acts are described as example implementations of such techniques.

Unless otherwise noted, all of the methods and processes described above may be embodied in whole or in part by software code modules executed by one or more general purpose computers or processors. The code modules may be stored in any type of computer-readable storage medium or other computer storage device. Some or all of the methods may alternatively be implemented in whole or in part by specialized computer hardware, such as FPGAs, ASICs, etc.

Conditional language such as, among others, "can," "could," "might" or "may," unless specifically stated otherwise, are used to indicate that certain examples include, while other examples do not include, the noted features, elements and/or steps. Thus, unless otherwise stated, such conditional language is not intended to imply that features, elements and/or steps are in any way required for one or more examples or that one or more examples necessarily include logic for deciding, with or without user input or prompting, whether these features, elements and/or steps are included or are to be performed in any particular example.

Conjunctive language such as the phrase "at least one of X, Y or Z," unless specifically stated otherwise, is to be understood to present that an item, term, etc. may be either X, or Y, or Z, or a combination thereof. Furthermore, in some cases 'A and B' could also mean 'A and/or B'.

Figure 15:
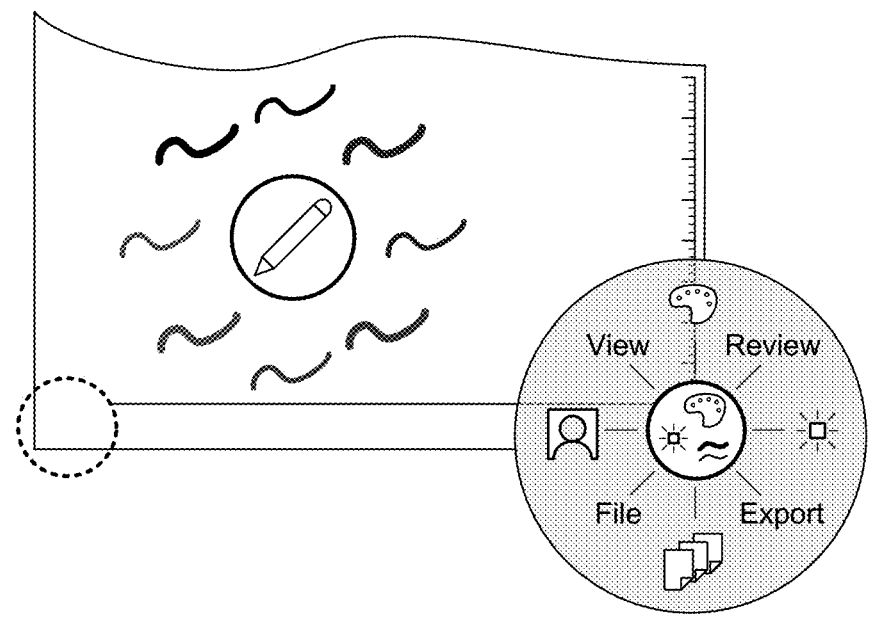
FIG. 15 depicts an exemplary expansion of a combined click-through and radial marking menu.
Figure 16:
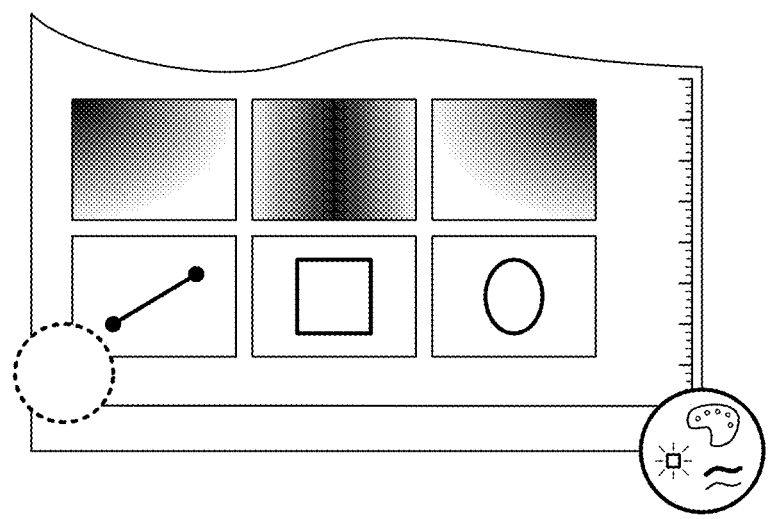
FIG. 16 depicts an exemplary menu accessible by an expansion of a combined click-through and radial marking menu employed in some of the multi-touch detection implementations described herein.
Figure 17:
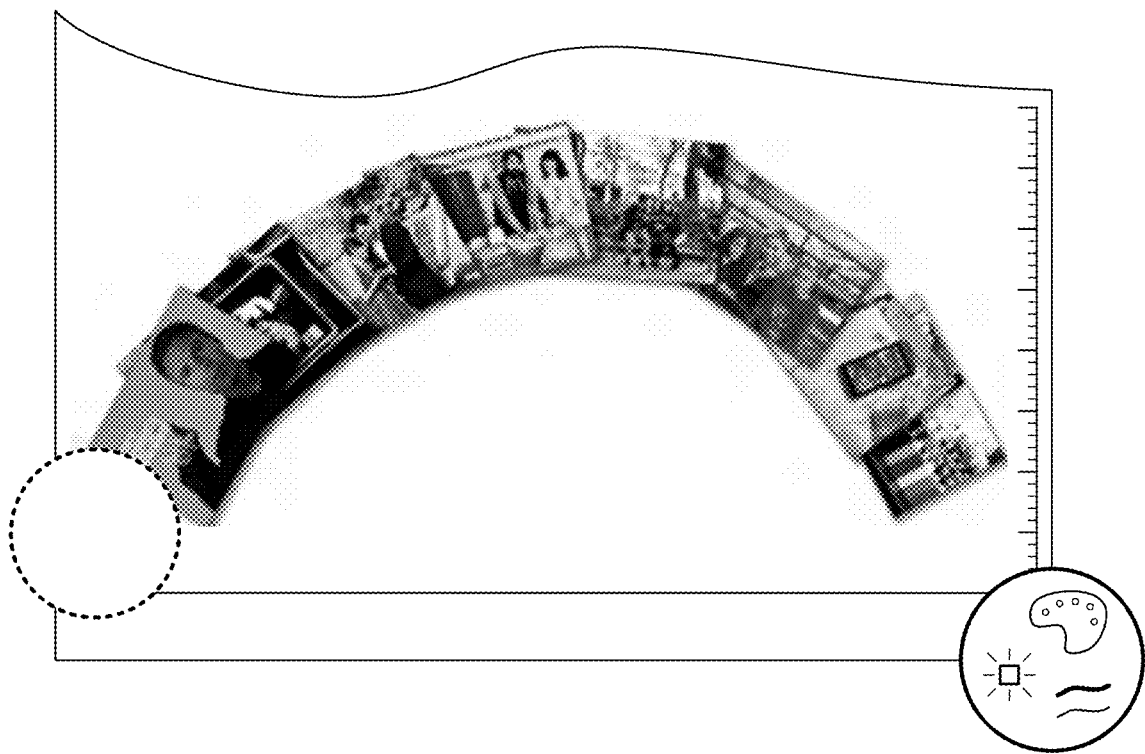
FIG. 17 depicts a combined click-through and radial menu from which photographs for a particular user can be selected.

Many variations and modifications may be made to the above-described examples, the elements of which are to be understood as being among other acceptable examples. For example, various types of menus and tools can be implemented using the multi-touch detection implementations described herein. For example, FIG. 15 depicts an exemplary expansion of a combined click-through and radial marking menu. FIG. 16 depicts an exemplary menu accessible by an expansion of a combined click-through and radial marking menu employed in some of the multi-touch detection implementations described herein. FIG. 17 depicts a combined click-through and radial menu from which photographs for a particular user can be selected. In some implementations these photographs can be retrieved from a computing cloud (e.g., Cloud). All such modifications and variations are intended to be included herein within the scope of this disclosure.

The invention claimed is:

1. A system comprising: a
touchscreen;
one or more processors;
a transceiver configured to receive signals from devices associated with specific users and send signals to the devices associated with the specific users, the devices associated with the specific users being separate devices from the system; and
a memory storing instructions that, when executed by the one or more processors, cause the one or more processors to perform operations comprising:
receiving data from a first device associated with a first user, the data from the first device associated with the first user comprising first acceleration data representative of an acceleration of a sensor resident in the first device associated with the first user and also comprising first identity data representative of an identity of the first user;
receiving data from a second device associated with a second user, the data from the second device associated with the second user comprising second acceleration data representative of an acceleration of a sensor resident in the second device and also comprising second identity data representative of an identity of the second user;
determining, based at least upon correlating a timing of a touch event with motion of the first device as determined from the first acceleration data and with motion of the second device as determined from the second acceleration data, whether the touch event correlates more strongly with the motion of the first device or the motion of the second device;
determining, based upon whether the touch event correlates more strongly with the motion of the first device or the motion of the second device and also the first identity data and the second identity data, whether the touch event represents an input performed by the first user or an input performed by the second user;
initiating a command personalized to the first user when the touch event is determined to be the input performed by the first user; and
initiating a command personalized to the second user when the touch event is determined to be the input performed by the second user.

2. The system of claim 1, wherein the stored instructions, when executed by the one or more processors, cause the one or more processors to perform operations comprising:
displaying at least one menu at a location of the touch event.

3. The system of claim 2, further comprising modifying least one object displayed by the touchscreen using the at least one displayed menu.

4. The system of claim 2, wherein the at least one menu moves with a movement of the touch event on the display as long as the touch event remains active due to the first user, the second user, or other object touching the display.

5. The system of claim 2, wherein a menu is personalized to the first user in response to initiating the command personalized to the first user.

6. The system of claim 2, wherein the at least one menu further comprises at least one radial menu that is used to modify an object that is underlying the at least one radial menu on the touchscreen.

7. The system of claim 2, wherein the touch event is determined to be caused by digits of the first user's hand or other objects touching the touchscreen, and wherein an object in an area between the digits or other objects is selected and modifiable by a menu that is associated with the area selected on the touchscreen.

8. The system of claim 2, wherein the touch event is determined to be caused by a touch event of the first user's hand or other objects touching the touchscreen, and wherein one or more objects in an area around the touch event are selected and modifiable by a menu that is associated with the selected area on the touchscreen.

9. The system of claim 8, wherein contours of boundaries of the menu are used as a tool to act on objects displayed on the touchscreen.

10. The system of claim 9, wherein the contours of the boundaries of the menu are modifiable by the first user.

11. The system of claim 1, wherein one or more commands to the first device are wirelessly sent, and wherein the one or more commands are targeted to the first device associated with a specific user.

12. The system of claim 1, wherein initiating the command personalized to the first user comprises determining a user privilege for the first user.

13. The system of claim 1, wherein the stored instructions, when executed by the one or more processors, cause the one or more processors to perform operations comprising:
modifying a menu displayed on the touchscreen based, at least in part, on the identity of the first user associated with the first device.

14. The system of claim 1, wherein the first device associated with the first user is a user wearable device.

15. A method enacted on a computing system comprising a touchscreen, one or more processors, and a transceiver configured to receive signals from devices associated with specific users and send signals to the devices associated with the specific users, the devices associated with the specific users being separate devices from the computing system, the method comprising:
receiving data from a first device associated with a first user, the data from the first device associated with the first user comprising first acceleration data representative of an acceleration of a sensor resident in the first device associated with the first user and also comprising first identity data representative of an identity of the first user;

receiving data from a second device associated with a second user, the data from the second device associated with the second user comprising second acceleration data representative of an acceleration of a sensor resident in the second device and also comprising second identity data representative of an identity of the second user;

determining, based at least upon correlating a timing of a touch event with motion of the first device as determined from the first acceleration data and with motion of the second device as determined from the second acceleration data, whether the touch event correlates more strongly with the motion of the first device or the motion of the second device;

determining, based upon whether the touch event correlates more strongly with the motion of the first device or the motion of the second device and also the first identity data and the second identity data, whether the touch event represents an input performed by the first user or an input performed by the second user;

initiating a command personalized to the first user when the touch event is determined to be the input performed by the first user; and initiating a command personalized to the second user when the touch event is determined to be the input performed by the second user.

16. The method of claim 15, further comprising displaying at least one menu at a location of the touch event, and wherein initiating the command personalized to the first user comprises displaying a menu personalized to the first user.

17. The method of claim 16, further comprising determining one or more privileges for the first user based upon the identity of the first user, and wherein initiating the command personalized to the first user comprises initiating a command based upon the one or more privileges determined.

18. A computer readable storage device storing instructions thereon that, when executed by a computing system comprising a touchscreen, one or more processors, and a transceiver configured to receive signals from devices, separate from the computing system, associated with specific users and send signals to the devices associated with the specific users cause the computing system to perform operations comprising:

receiving data from a first device associated with a first user, the data from the first device associated with the first user comprising first acceleration data representative of an acceleration of a sensor resident in the first device associated with the first user and also comprising data representative of an identity of the first user;

receiving data from a second device associated with a second user, the data from the second device associated with the second user comprising second acceleration data representative of an acceleration of a sensor resident in the second device and also comprising data representative of an identity of the second user;

determining, based at least upon correlating a timing of a touch event with motion of the first device as determined from the first acceleration data and with motion of the second device as determined from the second acceleration data, whether the touch event correlates more strongly with the motion of the first device or the motion of the second device;

determining, based upon whether the touch event correlates more strongly with the motion of the first device or the motion of the second device and also the data representative of the identity of the first user and the data representative of the identity of the second user, whether the touch event, whether the touch event represents an input performed by the first user or an input performed by the second user;

initiating a command personalized to the first user when the touch event is determined to be the input performed by the first user; and initiating a command personalized to the second user when the touch event is determined to be the input performed by the second user.

19. The computer readable storage device of claim 18, wherein the operations further comprise displaying at least one menu at a location of the touch event, and wherein initiating the command personalized to the first user comprises displaying a menu personalized to the first user.

20. The computer readable storage device of claim 18, wherein the operations further comprise determining one or more privileges for the first user based upon the identity of the first user, and wherein initiating the command personalized to the first user comprises initiating a command based upon the one or more privileges determined.

\* \* \* \* \*